US012758142B1

(12) United States Patent
Singal et al.

(10) Patent No.: US 12,758,142 B1
(45) Date of Patent: Oct. 13, 2026

(54) SYSTEM AND METHOD FOR PREDICTING MENOPAUSE SYMPTOMS AND INITIATING INTERVENTIONS

(71) Applicants: Manisha Singal, Washington, DC (US); Rengan Rajaratnam, Washington, DC (US)

(72) Inventors: Manisha Singal, Washington, DC (US); Rengan Rajaratnam, Washington, DC (US)

( * ) Notice: Subject to any disclaimer, the term of this patent is extended or adjusted under 35 U.S.C. 154(b) by 31 days.

(21) Appl. No.: 19/416,310

(22) Filed: Dec. 11, 2025

Related U.S. Application Data

(60) Provisional application No. 63/885,492, filed on Sep. 22, 2025.

(51) Int. Cl.

| | |
|---|---|
| ***A61B 5/00*** | (2006.01) |
| ***A61B 5/01*** | (2006.01) |
| ***A61B 5/0205*** | (2006.01) |
| ***A61B 5/024*** | (2006.01) |
| ***A61B 5/145*** | (2006.01) |
| ***A61B 5/1455*** | (2006.01) |
| ***A61B 5/16*** | (2006.01) |

(52) U.S. Cl.
CPC .......... *A61B 5/4306* (2013.01); *A61B 5/0002* (2013.01); *A61B 5/01* (2013.01); *A61B 5/02055* (2013.01); *A61B 5/02405* (2013.01); *A61B 5/14546* (2013.01); *A61B 5/14551* (2013.01); *A61B 5/165* (2013.01); *A61B 5/4815* (2013.01); *A61B 5/7275* (2013.01); *A61B 5/7475* (2013.01); *A61B 2560/0223* (2013.01); *A61B 2562/0271* (2013.01)

(58) Field of Classification Search
CPC ....... A61B 5/4306; A61B 5/0002; A61B 5/01; A61B 5/02055; A61B 5/02405; A61B 5/14546; A61B 5/14551; A61B 5/165; A61B 5/4815; A61B 5/7275; A61B 5/7475; A61B 2560/0223; A61B 2562/0271
See application file for complete search history.

(56) References Cited

U.S. PATENT DOCUMENTS

| | | | | |
|---|---|---|---|---|
| 2023/0084205 | A1* | 3/2023 | Kent | A61B 5/7435 600/301 |
| 2024/0016456 | A1* | 1/2024 | de Zambotti | A61B 5/02055 |
| 2024/0242837 | A1* | 7/2024 | Lee | G16H 10/60 |

* cited by examiner

*Primary Examiner* — Eugene T Wu

(57) ABSTRACT

A method, system and computer program product for predicting menopause related symptoms is described. The system receives biometric data streams of a user, environmental contextual data streams, and journal inputs, and accesses a previously established personalized biometric baseline. The system monitors the plurality of biometric data streams and contextual data streams for deviations from the personalized biometric baseline and using a predictive model, detects a pattern of physiological deviation from the personalized biometric baseline correlating with an impending menopause-related symptom, consequently predicting, an occurrence of the menopause-related symptom. Responsively, the system initiates an intervention action (presenting a notification of the predicted menopause-related symptom, or a recommendation of a mitigating activity, transmitting a control signal to an external device to mitigate the menopause-related symptom). The system employs federated learning and differential privacy to maintain data security, enables clinician-supervised remote patient monitoring, and generates documentation suitable for remote patient-monitoring reimbursement.

27 Claims, 6 Drawing Sheets

SYSTEM AND METHOD FOR PREDICTING MENOPAUSE SYMPTOMS AND INITIATING INTERVENTIONS

BACKGROUND

Technical Field

The present disclosure relates to health monitoring, prognostics and predictive analysis. More particularly, the present disclosure relates to computer implemented methods and systems for predicting menopausal and perimenopausal symptoms.

Related Art

Women commonly experience disruptive symptoms during the menopause transition, including vasomotor symptoms (hot flashes, night sweats), sleep disturbances, mood swings, and other physiological changes. A number of these symptoms may be identified or predicted based on biometric data such as heart rate, skin temperature, and so forth. Wearable health trackers, such as smartwatches, fitness bands, smart rings, and other sensors, can continuously collect biometric data that correlates with these symptoms. For example, a hot flash may be preceded or accompanied by an elevated heart rate and a sudden rise in skin temperature, while sleep disruptions can be reflected in changes in heart rate variability or restlessness during the night.

Despite the proliferation of consumer wearables and health apps, existing solutions for menopause management provide only limited insight. Conventional period trackers allow women to log symptoms and menstrual cycles; however, such solutions lack predictive analytics for menopause or perimenopause. Most wearable trackers and associated apps still offer only basic women's health tracking. However, such solutions offer retrospective tracking rather than forecasting symptoms. For instance, a user might manually note a hot flash after it occurs, but the system cannot reliably alert her in advance. Additionally, current devices typically consider few signals in isolation (such as skin temperature or heart rate), rather than combining multiple biometric and contextual signals that together could provide a more robust early-warning indicator.

Existing wearable and environmental-control systems primarily detect temperature or sweat changes after symptoms occur. They lack anticipatory modeling, biochemical correlation, and closed-loop feedback between prediction and intervention. Known solutions do not integrate hormonal or contextual variables, or only provide just-in-time therapeutic guidance from a clinician or physician within a supervised remote-monitoring framework.

Another challenge is tailoring predictions to individual variability. Menopause experiences vary widely among individuals; a "one-size-fits-all" threshold for detecting symptoms can result in false alarms or missed events due to personal differences in baseline heart rate, temperature, fitness level, and environment. A need exists for calibration of the system to each user's unique baseline physiology and habits. Furthermore, while some research efforts have explored detecting hot flashes via individual biomarkers (such as, heart rate patterns or skin conductance), these approaches may suffer accuracy issues in real-world settings or require uncomfortable sensors.

Further, solutions known in the art do not administer or suggest a suitable intervention once a symptom is detected or anticipated. Solutions known in the art rely on the user to respond (for example, turning on a fan during a hot flash).

Still further, data privacy is a key concern in health monitoring. Many women may be reluctant to share sensitive health data if not assured of privacy. Centralized cloud-based analysis of wearable data may pose risks of exposing personal information.

In light of the foregoing, there is a need for methods and/or systems to address these, and other shortcomings of women's health solutions known in the art.

SUMMARY

Embodiments presented herein are directed towards methods, systems and computer program products for early prognostics of symptoms of perimenopause and/or menopause. The embodiments described herein are also applicable to a broader class of hormone- or autonomic-related dysregulation conditions, including perimenopause, postpartum transition, and medication-induced vasomotor instability. Further, the embodiments described herein may also be applicable to other endocrine, metabolic, or cognitive transitions characterized by cyclical hormonal or autonomic patterns, for example, sleep disruption, stress reactivity, or metabolic instability, using the same predictive logic and data-fusion approach. Various embodiments presented herein leverage multi-sensor wearable data, personalized baselines, and advanced algorithms to provide such prognostics. It further seeks to integrate automated or guided interventions in a closed-loop manner to mitigate symptoms, while employing techniques to protect user privacy. This invention would empower users to better manage their menopause journey through foresight and timely action, improving comfort and health outcomes during this life stage.

Through integration of predictive modeling, multi-sensor fusion, physiological sensing, biochemical sensing, pharmacological and/or environmental context integration, multimodal correlation, federated learning, adaptive closed loop model tuning, and clinician-supervised feedback, the present disclosure advances digital women's healthcare from reactive symptom management to proactive precision monitoring. This following specification describes various embodiments for both consumer and clinical implementations of the system.

A method for predicting menopause-related symptoms and providing interventions is described. The method includes: receiving a plurality of biometric data streams of a user, including physiological measurements including heart rate, heart rate variability, body temperature, and blood oxygen saturation; receiving contextual data streams, including ambient temperature, and menstrual cycle information of the user; receiving from the user, a journal input including textual information describing the user's feelings, and/or the user's environmental context information; and accessing a personalized biometric baseline, wherein the personalized biometric baseline is previously established based on the plurality of biometric data streams. The method then monitors the plurality of biometric data streams and contextual data streams for deviations from the personalized biometric baseline; and detects, using a predictive model, a pattern of physiological deviation from the personalized biometric baseline correlating with an impending menopause-related symptom. The method then predicts, based on detecting the pattern of physiological deviation, and the journal input, an occurrence of the menopause-related symptom before it begins. Finally, responsive to the predicting, the method initiates an intervention action, wherein the intervention action includes at least one of: presenting to the user a notification of the predicted menopause-related symptom, transmitting a control signal to an external device to mitigate the menopause-related symptom, and presenting a recommendation to the user to perform a mitigating activity.

In some embodiments, the method further includes establishing the personalized biometric baseline in a calibration mode, wherein the calibration mode spans at least two days of data collection during which no menopause related symptoms are detected, and configuring the predictive model with the user's baseline circadian patterns and filtering out routine activities to reduce false positive predictions.

In some embodiments, the method further includes: updating at least one of the personalized biometric baseline, and the predictive model, based on at least one of the plurality of biometric data streams, the contextual data streams, the detected pattern of physiological deviation, the predicted menopause related symptom, and a user feedback pertaining to the predicted menopause related symptom; and transmitting the update to the predictive model to a remote learning and management server.

In some embodiments, the method further includes: retrieving the predictive model from a remote server; determining updated model parameters of the predictive model, based on at least one of the plurality of biometric data streams, the detected pattern of physiological deviation, the predicted menopause related symptom, and a user feedback confirming or denying occurrence of the predicted menopause related symptom; and transmitting the updated model parameters to the remote server, wherein the predictive model is a machine learning model or an artificial intelligence model.

In some embodiments, the method further includes: analyzing prior intervention actions associated with respective prior predictions of respective prior menopause related symptoms, and severity of the respective prior menopause related symptom; based on the analyzing, identifying a recommended intervention action wherein the recommended intervention action is the prior intervention action with the least severity of the respective prior menopause related symptom; and updating the predictive model, based on the identifying.

In some embodiments, the method further includes: prompting the user to provide a confirmation of occurrence or a severity rating of the predicted menopause related symptom; receiving the user feedback comprising the confirmation of occurrence or the severity rating of the predicted menopause related symptom; identifying the predicted menopause related symptom as a true positive or a false positive; and updating at least one of the personalized biometric baseline, and the predictive model, based on the identifying.

In some embodiments, the method further includes: mapping the predicted symptom and the intervention action to corresponding ones of Current Procedural Terminology (CPT) codes; generating documentation suitable for remote patient-monitoring reimbursement, wherein the documentation includes at least one of the biometric data streams, the contextual data streams, the menopause related symptom prediction, a user feedback on the menopause related symptom prediction, and a user compliance metric; and transmitting to a remote patient monitoring system, the generated documentation and the CPT codes.

In some embodiments, the method further includes: receiving from the user, a journal input including textual information describing the user's feelings, and/or the user's environmental context information; natural language processing the journal input, to identify natural language features including emotional tone, symptom-intensity descriptors, and temporal references; and predicting the occurrence of the menopause-related symptom before it begins further based on the natural language features identified from the journal input.

In some embodiments, the method further includes selecting the intervention action from a plurality of prior intervention actions, wherein the selected intervention action is associated with the largest suppression of intensity of the menopause related symptom.

In some embodiments, the plurality of biometric data streams of a user further include biochemical measurements including hormone levels, including at least one of estradiol, progesterone, luteinizing hormone, cortisol, or thyroid markers.

In some embodiments, the menopause-related symptom includes one of a hot flash or night sweat, the pattern of physiological deviation includes an abrupt increase in the user's skin temperature and heart rate relative to the personalized biometric baseline, and the intervention action includes activating a cooling mechanism to counteract the hot flash.

In some embodiments, the method further includes: the menopause-related symptom includes one of insomnia or sleep disturbance, mood swing, anxiety episode, heart palpitations, and fatigue, and the contextual data stream includes sleep quality data or stress level data of the user.

Various embodiments also discuss systems and modules that perform the aforementioned method. Further, various other embodiments also discuss computer program products, having computer readable instructions stored on a computer readable medium, which when executed by a computer system comprising a processor, cause the processor to execute the aforementioned method.

DETAILED DESCRIPTION

Figure 1:
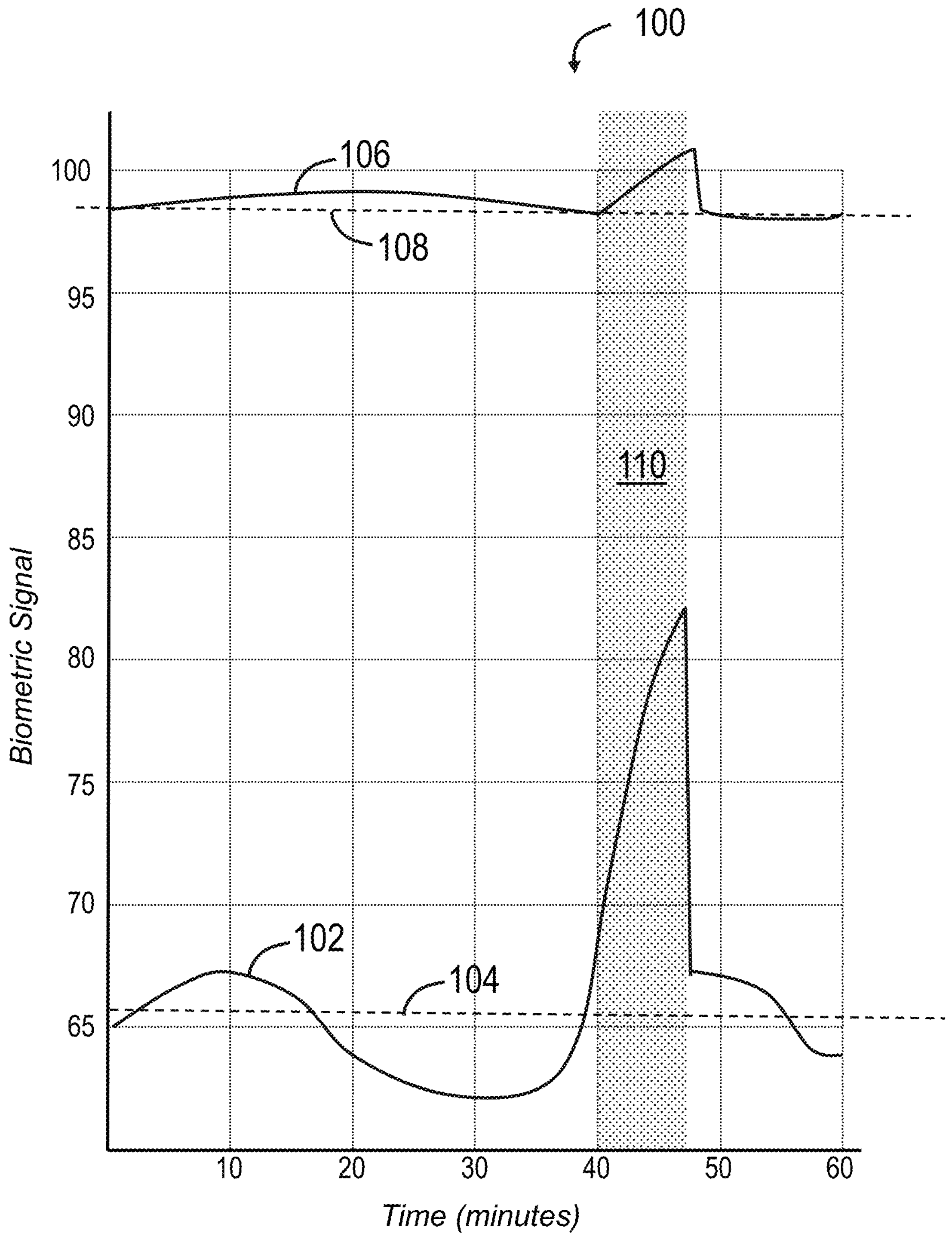
FIG. 1 is a graph illustrating exemplary biometric signal patterns leading up to a menopause related symptom, according to one embodiment.

Prior to describing the invention in detail, definitions of certain words or phrases used throughout this patent document will be defined: the terms "include" and "comprise", as well as derivatives thereof, mean inclusion without limitation; the term "or" is inclusive, meaning and/or; the phrases "coupled with" and "associated therewith", as well as derivatives thereof, may mean to include, be included within, interconnect with, contain, be contained within, connect to or with, couple to or with, be communicable with, cooperate with, interleave, juxtapose, be proximate to, be bound to or with, have a property of, or the like; Definitions of certain words and phrases are provided throughout this patent document, and those of ordinary skill in the art will understand that such definitions apply in many, if not most, instances to prior as well as future uses of such defined words and phrases.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Although the operations of exemplary embodiments of the disclosed method may be described in a particular, sequential order for convenient presentation, it should be understood that the disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment and may be applied to any embodiment disclosed herein. Moreover, for the sake of simplicity, the attached figures may not show the various ways in which the disclosed system, method, and apparatus can be used in combination with other systems, methods, and apparatuses.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments. These features and advantages of the embodiments will become more fully apparent from the following description and apportioned claims, or may be learned by the practice of embodiments as set forth hereinafter.

While some advantages have been described above and through the remainder of the present disclosure, it shall be appreciated that these advantages are merely exemplary and the review analysis system described herein may have other advantages. The system architecture and methods described herein are applicable not only to menopause but to a broader class of hormone- or autonomic-related dysregulation conditions, including perimenopause, postpartum transition, and medication-induced vasomotor instability.

Embodiments presented herein provide specific improvements to the functioning of computer-implemented health monitoring systems. Instead of applying fixed thresholds to raw sensor data, the system uses a personalized baseline model, multi-modal sensor data fusion including the user's biometric data, user's context information, and the user's subjective feelings and/or experience (through the journal inputs), and a prediction engine configured to detect precursor patterns of menopause-related symptoms before onset. By dynamically adjusting decision thresholds based on the user's learned biometric (physiological and/or biochemical) information, and user's context (activity, environment, location), and by automatically triggering device-level interventions without manual rule authoring, the system reduces false positives, reduces unnecessary alerts, and improves the stability and accuracy of symptom prediction compared to conventional rule-based monitoring systems.

Embodiments presented herein pertain to methods, systems, and computer program products for predicting menopause related symptoms, and suggesting and/or effecting remedial measures (in other words, intervention actions) to manage or reduce the severity of the symptom when it occurs. Unlike threshold-based approaches reacting to signal spikes, the disclosed methods and systems employ multivariate temporal modeling to anticipate events and initiate proactive intervention. Embodiments presented herein enable a smarter, closed-loop system that not only predicts an oncoming symptom but also automatically or semi-automatically triggers intervention actions or relief measures-such as activating a cooling device, sending a reminder to hydrate, adjusting room temperature via a smart thermostat, or initiating a calming routine—to help the user get ahead of the symptom, among other remedial measures. Intervention actions include but are not limited to environmental adjustments (temperature, airflow, lighting), wearable actuation, micro-vibration feedback, biofeedback cues, medication prompts, and behavioral coaching. In various embodiments, intervention actions also include one or more of pharmacologic, nutraceutical, or digital-therapeutic interventions. Further, embodiments presented herein incorporate privacy-preserving learning (for example, through federated machine learning), allowing the collective data from many users to train better predictive models without compromising the privacy of each user's raw data. Some embodiments presented herein may be implemented as a direct-to-consumer wellness mode, wherein the system monitors the patient, predicts menopause related symptoms, and suggests and/or effects remedial interventions for the patient. Some other embodiments presented herein may be implemented as a clinically supervised mode integrated with remote patient monitoring (RPM) and care management reimbursement workflows. Some embodiments presented herein may include natural-language processing (NLP) of free-text symptom journaling yield individualized prediction models.

Turning now to the figures, various embodiments of a review analysis system are described herein.

FIG. 1 is a graph 100 illustrating exemplary biometric signal patterns leading up to a menopause related symptom, according to one embodiment. Graph 100 plots a heart rate curve 102, a heartrate baseline 104, a temperature curve 106, a temperature baseline 108, and a predicted hot flash window 110. The magnitude or level is indicated on the vertical axis (i.e. the y-axis), and the time elapsed is plotted on the horizontal axis (i.e. the x-axis). Graph 100 may now be explained in conjunction with an example scenario of a perimenopausal user's biometric signals.

The graph 100 may plot the heart rate and body temperature of a perimenopausal user, for example. In some embodiments, the heart rate and the body temperature measurements may be measured by the same device. In some other embodiments, the heart rate and the body temperature may be measured by different devices. Some suitable devices for measuring the heart rate and the body temperature may include, without limitation, smart watches, smart rings, biometric measurement arm bands, biometric measurement chest straps, smart mattresses and smart beds designed to measure physiological parameters of the users, smart thermal cameras, and so forth.

A menopause prognostic system may first undergo a calibration period, during which the system monitors, and logs the user's heart rate, and body temperature pattern. The calibration period may last about a week or two weeks, for example. Over the calibration period, the system learns the heart rate baseline, and the body temperature baseline values. For example, in graph 100, the menopause prognostic system learns: a resting heart rate baseline of 60 bpm, with a sleep heart rate variability (HRV) of 40 ms SDNN (standard deviation of NN intervals), a skin temp baseline of 33° C. with ±0.5° C. daily variation, and so forth.

During the calibration period, the user may manually log hot flashes that she experiences, along with a timestamp indicating at least the approximate time of occurrence of the hot flash. Further, the menopause prognostic system may also identify deviations from the biometric baselines, such as the heart rate baseline, and the body temperature baseline, learned up to that point in time. The menopause prognostic system may then correlate the identified deviations, with the user logged hot flashes, to learn a pattern of physiological markers, that help predict the hot flash event. For example, the user logs a few hot flashes she experienced, typically around mid-afternoon and some at night.

After the calibration period concludes, the menopause prognostic system enters into a prognostic mode, during which the menopause prognostic system predicts menopause symptoms such as hot flashes, night sweats, insomnia or sleep disturbance, mood swing, anxiety episode, heart palpitations, fatigue, and so forth.

For example, one afternoon, around 2:00 PM, the user's wearable data starts to show her skin temperature rising at a rate of 0.3° C. over the last minute, and her heart rate went from 65 to 82 bpm in that same minute, even though she's just sitting at her desk. The ambient room temperature is steady at 22° C. The system's model flags this pattern as matching the profile of a pre-hot-flash onset (since during her past logged hot flashes, a similar spike was recorded). By 2:01 PM, the model's hot flash risk score exceeds the threshold. Later that night, at 3:00 AM, the system detects signs of a possible night sweat coming: her heart rate, which had been 55 bpm, jumps to 70 bpm, and her motion sensor indicates she's stirring. The model gives an early warning of a night-time hot flash.

The menopause prognostic system may then provide one or more intervention actions, such as, but not limited to, presenting to the user a notification of the predicted menopause-related symptom, transmitting a control signal to an external device to mitigate the menopause-related symptom, and presenting a recommendation to the user to perform a mitigating activity. Intervention actions include but are not limited to environmental adjustments (temperature, airflow, lighting), wearable actuation, micro-vibration feedback, biofeedback cues (for example, visual feedback, auditory feedback, tactile feedback, or a combination thereof, prompting the user to correct adverse conditions such as stress, anxiety, and so forth), medication prompts, and behavioral coaching. In various embodiments, intervention actions also include one or more of pharmacologic, nutraceutical, or digital-therapeutic interventions.

For example, in some embodiments, an app of the menopause prognostic system may immediately issue a gentle vibration and notification: "Hot flash predicted—cooling now."

In some other embodiments, the menopause prognostic system may transmit a control signal to an external device. For example, transmitting a control signal to cause a wearable cooling device starts a cooling pulse cycle. The menopause prognostic system may alternatively, or additionally, transmit a signal to the user's smart thermostat to lower room temperature by 2° C. The menopause prognostic system may cause an air conditioning unit to direct airflow towards the user to facilitate rapid spot cooling. The menopause prognostic system may transmit a control signal to a smart fan to turn up the fan speed and direct airflow towards the user to facilitate cooling.

In still other embodiments, the app of the menopause prognostic system may present a recommendation to the user, for example, to have a cool drink to cool down. Alternatively, or additionally, the menopause prognostic system may cause a non-visual alert, such as a vibration to a smart wearable device, or a sound played back from a bed side speaker, to prompt the user to take mitigating action—for instance, to remove a blanket she is currently covering herself with.

As a result of the interventions before or at the onset of the menopause symptom the severity or intensity of the hot flash may be reduced. While the user still experiences the hot flash, her peak skin temperature, and therefore her discomfort is reduced. Further, the hot flash passes faster than without any such remedial interventions. Further, during the night, a fully awaken disruptive night sweat may be avoided by addressing it in the early phase, and thus her sleep quality remains higher. These examples demonstrate how the system may anticipate and react to menopause symptoms, improving the user's quality of life.

Figure 2:
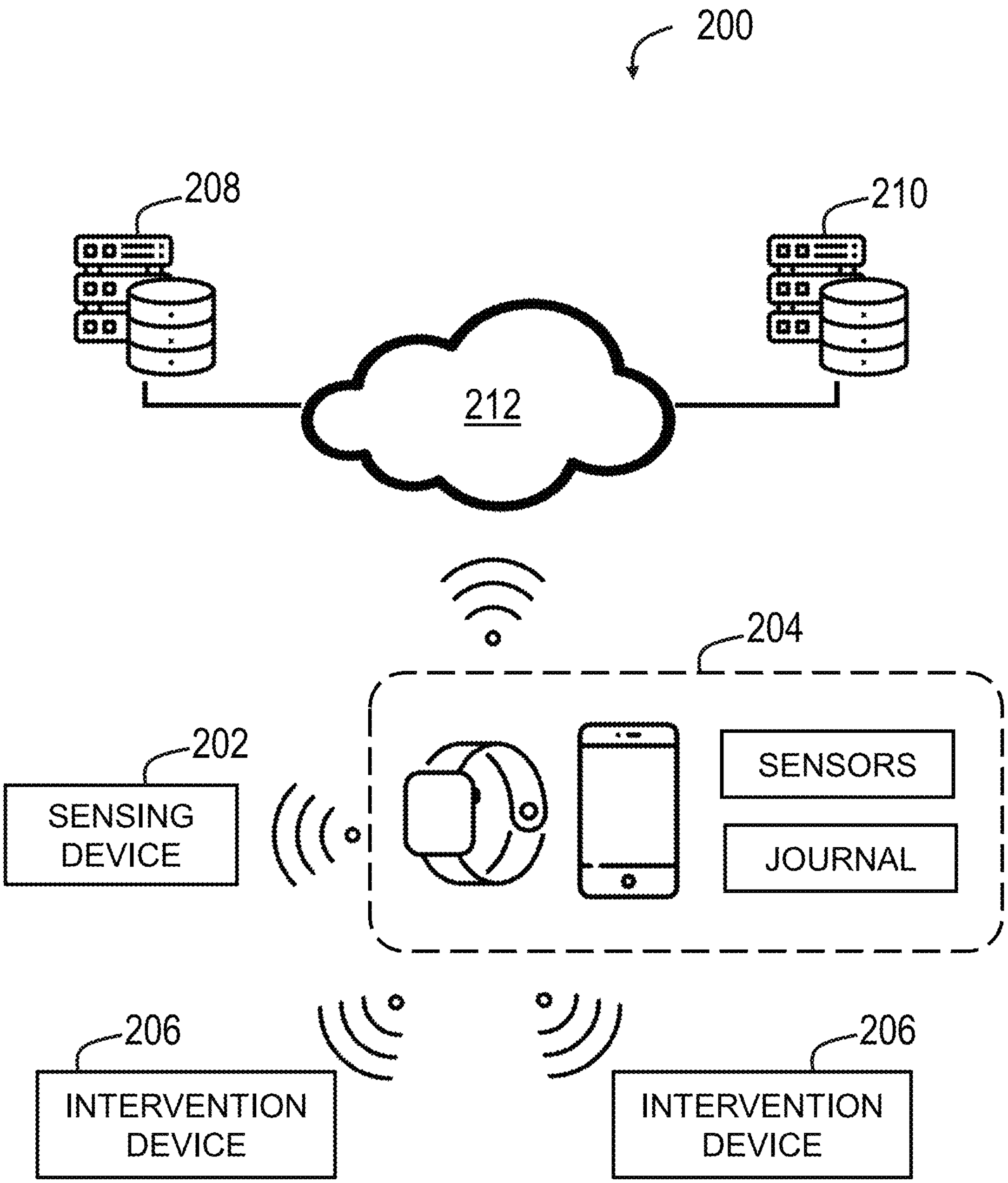
FIG. 2 illustrates an exemplary environment, within which a system for predicting menopause symptoms, according to one embodiment.

FIG. 2 illustrates a block diagram of an exemplary environment 200, within which a system for predicting menopause symptoms operates, according to one embodiment. The environment 200 includes sensing devices 202, a user device 204, intervention devices 206, a learning and modeling server (LMS) 208, a remote patient monitoring server (RPMS) 210, and a network 212.

Sensing devices 202 are configured to capture biometric data of the user, and/or context data. The biometric data may include physiological information of the user, and biochemical information of the user.

The sensing devices 202 include, without limitation, wearable devices, smart home devices, and home automation devices. Common examples of wearable devices include, without limitation, smartwatches (worn on the wrist), smart rings (worn on a finger), fitness bands, patches or smart garments applied to the skin, or even earbud-style biosensors. Some examples of smart home devices include, without limitation, smart mattresses, smart beds, smart pillows, smart blankets, and so forth, capable of monitoring physiological data of the user.

The sensing devices 202 may include sensors such as, but not limited to: a photoplethysmography (PPG) sensor for heart rate and heart rate variability; a temperature sensor for skin or body temperature (for example, wrist temperature); an accelerometer/gyroscope for detecting motion, activity level, and sleep posture; a pulse oximeter for measuring $SpO_2$; a respiration sensor (which might be derived from PPG or motion data to estimate breathing rate); a peripheral perfusion sensor (for example, a PPG sensor) and potentially electrodermal activity (EDA) sensors for skin conductance indicating sweat response. Such sensing devices 202 are configured to capture the biometric data streams, including physiological measurements, and/or biochemical measurements of the user. In this description, biometric data streams may refer to either the physiological measurements of the user, the biochemical measurements of the user, or a combination of the two. Additional digital biomarkers such as voice tone, facial thermography, or peripheral perfusion data may also be used to infer autonomic or hormonal state changes. For such biomarkers, the sensing devices 202 may include, for example, microphones, cameras, infrared or thermal cameras, and the like. A hardware, firmware, or software module may be part of such sensing devices 202 to infer autonomic or hormonal state changes, based on the digital biomarkers.

In one embodiment, the sensing device 202 may be a biochemical monitoring device, such as a continuous hormone monitoring sensor. Such hormone monitoring devices may be used as a semi-persistent patch device, which may be adhered to the user's body, and may monitor hormone levels of the user for a limited period of time—for example, one week or two weeks. Such devices may monitor hormonal levels such as, but not limited to, estradiol, progesterone, luteinizing hormone (LH), cortisol, thyroid related biomarkers, follicle-stimulating hormone (FSH), luteinizing hormone (LH), inhibin B, dehydroepiandrosterone (DHEA), and so forth. Such biomarkers may be measured periodically or continuously via blood, saliva, sweat, or interstitial fluid sensors. Incorporation of these biochemical signals enables modeling of endocrine transitions and stress-related dynamics associated with menopausal symptom onset.

In certain embodiments, data related to a user's hormone replacement therapy (HRT) regimen, including type, dosage, route of administration, and adherence patterns may also be included in the biochemical data. These parameters can be incorporated as contextual variables within the predictive model to forecast symptom occurrence or treatment response. In some embodiments, the sensing device 202, such as the continuous hormone monitoring sensor may have the HRT regimen information saved therein, by a clinician, a healthcare professional, the continuous hormone sensor provider, pharmacist, or the like. In other embodiments, the HRT regimen information may be transmitted to the continuous hormone monitoring sensor, from a remote server (for example, from a clinic, a hospital, a pharmacist, insurance provider, or the like). In still other embodiments, the HRT regimen information may be directly transmitted to, and/or saved on the user device 204, in mechanisms similar to those described above, with respect to the continuous hormone monitoring sensor.

Further, sensing devices 202 may include sensors such as, but not limited to, accelerometers/gyroscopes for detecting motion and activity levels of the user. Such sensing devices 202 are configured to capture the activity context data of the user. Sensing devices 202 may also capture user's sleep stage information, for example, as a derived parameter during sleep based on activity (i.e. motion or acceleration data of the user), and heart rate. Further, sensing devices 202 may also include ambient temperature sensors for detecting the ambient temperature of the room within which the user is presently located, ambient humidity sensors for detecting the humidity of the room within which the user is presently located, location sensors to detect the location of the user—for example, within a particular room of a house or office, whether the user is in a particular building-such as at home, at the office, in a mall, or whether the user is in a transportation medium, such as a train, a taxi, an airplane, and elevator, and so forth. Such sensing devices 202 are configured to capture the environmental context data of the user.

The sensing devices 202 may further include a processor and memory to collect the data signals at regular intervals (for example, heart rate and temperature every second or a few seconds, activity context data signals every few seconds, and environmental context data signals every minute or every few minutes), and a wireless transceiver configured to communicate with the user device 204, or other sensing devices 202. The sensing devices 202 may further process the received biometric and user context data signals to derive further parameters, such as the sleep stage during the user's sleep. For example, the sensing device 202 may derive the user's sleep stage (light sleep, deep sleep, REM sleep), based on the user's activity context data (i.e. the user's motion and/or acceleration data), and the user's heart rate data. The sensing devices 202 may also capture the time of day information, and utilize it for timestamping the various received data streams, and for further processing by the user device 204. The sensing devices 202 may use wireless communication standards such as, but not limited to, Bluetooth, Bluetooth Low Energy (BLE), Zigbee, IEEE 802.11 Wi-Fi, cellular network, or any other wireless communication protocols. Further, the sensing devices 202 may communicate with the user device 204 through connected APIs. The software design of the firmware of the sensing devices 202 may conform to FDA GMLP and medical-device standards (IEC 62304, ISO 14971) to facilitate regulatory compliance. In some embodiments, the sensing devices 202 may implement the Fast Healthcare Interoperability Resources (FHIR) standard, Health Level Seven (HL7) standard or another comparable interoperability standards, to communicate with the user device 204. The sensing devices 202 may export structured data using FHIR or HL7 standards for Electronic Health Records (EHR) and Remote Patient Monitoring (RPM) integration, maintaining audit trails consistent with Software as a Medical Device (SaMD) frameworks.

In various embodiments, one or more sensing devices 202 are integral to the user device 204. For example, where the user device 204 is a smartphone or a smart watch or wearable health tracking device, or any similar device, the sensing device 202 may be integrated into the user device 204, in the form of one or more sensors described above.

The user device 204 is configured to be function as the core of the menopause symptoms prediction system. The user device 204 may communicate with the sensing devices 202, to retrieve or receive biometric data (including physiological and biochemical data) and user context data (including the activity context data, environmental context data, or both), as measured by the sensing devices 202. The user device 204 may be configured to capture the biometric data and user context data in respective time series data streams. In other words, the user device 204 may capture one or more biometric data streams corresponding to the various physiological measurements and biochemical measurements made by the sensing devices 202, and one or more contextual data streams corresponding to the activity context information, and environmental context information measured by the sensing devices 202. The user device 204 may include, for example, a smartphone, a tablet computer, a personal computer, and so forth.

The user device 204 may include a processor and memory to collect the biometric data, and contextual data at regular intervals (for example, heart rate and temperature every second or a few seconds, activity context data signals every few seconds, and environmental context data signals every minute or every few minutes), and a wireless transceiver configured to communicate with the sensing devices 202, and the intervention devices 208. The user device 204 may further process the received biometric and user context data signals to derive further parameters, such as the sleep stage during the user's sleep. For example, the user device 204 may derive the user's sleep stage (light sleep, deep sleep, REM sleep), based on the user's activity context data (i.e. the user's motion and/or acceleration data), and the user's heart rate data. The user device 204 may also capture the time of day information, and utilize it for timestamping the various received data streams, and for further processing by the user device 204. The user device 204 may use wireless communication standards such as, but not limited to, Bluetooth, Bluetooth Low Energy (BLE), Zigbee, IEEE 802.11 Wi-Fi, cellular network, or any other wireless communication protocols. Further, the user devices 204 may communicate with the user device 204 through connected APIs. The software design of the user device 204 may conform to FDA GMLP and medical-device standards (IEC 62304, ISO 14971) to facilitate regulatory compliance. In some embodiments, the user device 204 may implement the Fast Healthcare Interoperability Resources (FHIR) standard, Health Level Seven (HL7) standard, or another comparable interoperability standard, to communicate with the sensing devices 202, and the intervention devices 208. The user device 204 may export structured data using FHIR or HL7 standards for Electronic Health Records (EHR) and Remote Patient Monitoring (RPM) integration, maintaining audit trails consistent with Software as a Medical Device (SaMD) framework.

The user device 204 may operate in a consumer mode, or in a clinical mode. The consumer mode may be seen as a personal wellness mode, wherein the user utilizes the user device 204 without a prescribed medical or clinical requirement. Such a mode may provide all the benefits of prediction of menopause related symptoms, without the compliance, prescription, and/or insurance requirements for a clinical usage scenario. The user device 204 may alternatively, operate in a clinical mode, wherein the user device 204 not only provides prediction of the menopause related symptoms to the user, but also performs other functions related to a clinical remote patient monitoring scenario such as logging user biometric information, logging user journal inputs, identifying CPT codes for the user's symptoms and interventions suggested and/or administered, reporting to the RPMS 210 the logged user information, and the identified CPT codes. The user device 204 may be configurable to be operable in either the consumer mode, or the clinical supervised mode, for example, by a configuration in an application running on the user device 204. The user device 204 may include an operational toggle permitting transition between a consumer wellness mode and a clinical mode. The transition may be triggered by a configuration flag, clinician credential, or integration token. In the clinical mode, the system activates compliance logging, timestamps clinician-reviewable events, and securely transmits encrypted CPT-coded reports to the RPMS 210 for reimbursement processing.

The user device 204 runs a dedicated menopause monitoring module (illustrated in FIG. 3) configured to communicate with the sensing devices 202, communicate with intervention devices 206, and communicate with the learning and modelling server 208. The user device 204 processes the biometric (physiological and/or biochemical) signal information and user context information received from the sensing devices 202, and the prediction models and/or baseline information from the learning and modelling server 208, to provide an early warning of an impending menopause related symptom, before it occurs. Further, the user device 204 may: aggregate and store the incoming data streams from the sensing devices 202; and provide a user interface for the user to view insights, configure settings, and provide feedback. In one embodiment, the user device 204 performs multi-modal processing of the biochemical measurements together with the physiological information and the user context information to enhance accuracy of symptom prediction and to identify pre-symptomatic hormonal fluctuations predictive of upcoming menopause-related events. In another embodiment, the user device 204 may further perform multi-modal processing of the physiological information and the user context information with HRT regiment adherence and response over time, to generate predictions of therapeutic efficacy or recommend timing adjustments, and improve prediction accuracy.

In addition to, or alternative to the biometric information, and the user context information, the user device 204 may also account for metabolic or treatment-related factors including BMI, insulin resistance, metabolic syndrome, thyroid status, cancer-related treatments, and/or HRT regimen adherence and response over time. Adjusting for these allows accurate modeling of endocrine and thermoregulatory patterns across varied health states. The predictive model may further incorporate genetic, immunologic, or inflammatory factors known to influence hormone balance and symptom patterns, including polymorphisms in estrogen pathways, autoimmune thyroid disorders, and post-infectious inflammatory states. Certain embodiments analyze neurophysiologic and autonomic markers-HRV, EDA, pupil response-linked to hypothalamic thermoregulation and stress. Modeling these pathways enables early detection of autonomic instability preceding vasomotor, sleep, or mood symptoms. The user device 204 may integrate gut-microbiome or circadian data such as actigraphy, HR, body temperature, or melatonin proxies. Shifts in these markers can indicate changes in hormonal regulation relevant to symptom prediction. Digital or behavioral indicators of mood and cognition (reaction time, speech, self-report) and long-term metrics like bone density, muscle mass, or cardiovascular markers may be incorporated to track broader health impacts. Such markers may be provided to the user device 204 by structured or unstructured data sources, such as laboratories, clinics, healthcare providers, hospitals, and so forth. In some embodiments, the predictive models include, for example, but without limitation, a recurrent neural network (RNN), transformer-based temporal sequence model, or an ensemble thereof configured to process multimodal time-series data and generate individualized risk probabilities. The predictive model may include a personalization loop wherein model parameters may be dynamically adjusted based on longitudinal (i.e. time series) user data, thus improving predictive accuracy and intervention timing over time.

In one embodiment, the user device 204 accepts data from a plurality of heterogeneous sensing devices 202, including wearable devices, environmental sensors, and network-connected actuators. The user device 204 normalizes the incoming data streams into a unified time-series schema, allowing the predictive model to remain device-agnostic while dynamically weighting signal reliability based on sensor type and context.

In some embodiments, user-provided narratives, symptom check-ins, and short journal prompts are processed as natural-language inputs that complement the biometric data signals, and contextual data signals. In various embodiments, the user device 204 may also include a journal application, configured to allow the user to input symptom narratives in free text. The user may use the journal application to indicate to the user device 204, what the user feels, prior to, during, or after the occurrence of a menopause related symptom. The user device 204 may then employ language processing such as natural language processing, machine learning, artificial intelligence, and/or large language models (LLM) to process the user's journal inputs. In some embodiments, the journal application applies natural-language-processing (NLP) algorithms, including tokenization, entity recognition, and sentiment analysis, to convert user-entered free-text symptom narratives into structured, time-stamped data features, including but not limited to emotional tone, symptom-intensity descriptors, and temporal references. The user device 204 may thus accept user reported symptoms, and/or periodic or aperiodic user logs or surveys about the user's quality of life including, for example, the user's mood, sleep quality, aches and pains, and so forth. The user device 204 may then utilize language processing (as described above), to extract and log information about the symptoms, such as, but not limited to, severity of the symptoms, typical timing of the symptoms, frequency of occurrence of the symptoms, trends of occurrence of the symptoms, and so forth. In various embodiments, the journal application also captures the time stamp indicating the time at which the user experiences the reported symptoms. Such a time stamp may be automatically captured by the journal application or may be input by the user.

In one embodiment, the user device 204 may correlate derived information about the user's symptoms from natural-language journal entries with biometric data and environmental context information to improve prediction accuracy for menopause-related symptoms. Extracted linguistic features, including emotional tone, symptom-intensity descriptors, and temporal references, are numerically encoded and fused with biometric and contextual signals within the predictive model. In some embodiments, the numerical encoding includes assigning a score to the extracted language features, or a probability value to the extracted language features. The user device 204 may then dynamically recalibrate prediction thresholds of the prediction model based on the numerical encoding of the extracted language features, thereby refining model sensitivity to the user's subjective experience. In some embodiments, the user device 204 may further map recognized symptoms and corresponding interventions to Current Procedural Terminology (CPT) codes, enabling automatic clinical documentation and reimbursement integration within remote patient-monitoring workflows.

The user device 204 may employ a natural-language processing engine trained on anonymized patient narratives and menopause symptom corpora to extract linguistic sentiment vectors. These vectors are weighted alongside physiologic indicators using reinforcement learning, allowing the natural-language processing model to assign relative importance to subjective and objective symptom data. This integration improves explainability by enabling each menopause symptom prediction to be traced to contributing linguistic and biometric features.

For example, a user's evening journal entry includes "wearing too many layers, feeling flushed, can't cool down," with a negative emotional tone. Within 120 seconds, the model's disruption risk increases due to elevated skin temperature and reduced HRV relative to the user's baseline. The user device 204 may then issue a pre-emptive alert and triggers a connected cooling device for 5 minutes. The event is logged with a recommended CPT code for clinician review in remote patient-monitoring workflows.

In various embodiments, the user may own more than one user device 204. In such an embodiment, the plurality of user devices 204 may also be synchronized among each other, as well as connected to the sensing devices 202, and the intervention devices 206, and communicably connected to the LMS 208, and RPMS 210. Any combination of connectivity between the plurality of user devices 204 and the other devices and servers in environment 200 are possible. For example, some of the plurality of user devices 204 may be communicably connected to the LMS 208 and the RPMS 210, while some of the plurality of user devices 204 may only be connected locally to the sensing devices 202 and the intervention devices 206. However, all of the plurality of user devices 204 of the user may be communicably connected to one another.

Connected intervention devices 206 represent any external devices or systems that the invention can control or prompt to help manage a symptom. Examples include: an intelligent cooling device 206*a* (such as a wristband that provides a cool sensation or a smart cooling pad on a bed), a smart thermostat 206*b* for room temperature adjustments, smart lights (which can be dimmed or color-shifted to promote calm during an episode or to avoid bright light during a nighttime hot flash), a smart speaker or alarm (to deliver guided meditation or breathing exercises), or even medication delivery systems (like a reminder or an automatic dispenser if applicable for certain treatments). These connected devices may be integrated through IoT protocols (Wi-Fi, ZigBee, Bluetooth) and have their own APIs. The intervention devices 208 may further include a processor and memory, and a wireless transceiver configured to communicate with the user device 204, or sensing devices 202. The intervention devices 208 may use wireless communication standards such as, but not limited to, Bluetooth, Bluetooth Low Energy (BLE), Zigbee, IEEE 802.11 Wi-Fi, cellular network, or any other wireless communication protocols. Further, the intervention devices 208 may communicate with the user device 204 through connected APIs. In some embodiments, the intervention devices 208 may implement the Fast Healthcare Interoperability Resources (FHIR) standard, Health Level Seven (HL7) standard, or another comparable interoperability standards, to communicate with the user device 204. The user's smartphone or the server can send commands to these devices when triggered by the prediction logic. For instance, if a hot flash is predicted, the system might send a command to the smart thermostat to immediately lower the bedroom temperature by a few degrees or turn on an AC unit.

In some embodiments, the intervention devices 206 may also be integral to the user device 204 for example, a Peltier element on a wearable device to provide a cooling sensation to the user. In some other embodiments, the intervention device 206 may be the user device 204 itself, and provides visual, audible, and/or tactile alerts to the user such as recommended remediation measures for a predicted menopause related symptom.

The intervention devices 206 may be any other devices configured to provide appropriate intervention actions. Intervention actions include but are not limited to environmental adjustments (temperature, airflow, lighting), wearable actuation, micro-vibration feedback, biofeedback cues, medication prompts, and behavioral coaching. In various embodiments, intervention actions also include one or more of pharmacologic, nutraceutical, or digital-therapeutic interventions.

In some embodiments, the intervention devices 206 may include environmental-control systems, or any connected device capable of modifying ambient conditions, including but not limited to HVAC systems, fans, lighting, or wearable cooling accessories. No specific hardware configuration is required for implementation. The control logic of the intervention devices 206 may further optimize environmental adjustments to minimize energy consumption while maintaining physiologic stability.

In some embodiments, the smartphone application performs all data analysis locally (for privacy and real-time speed). The predictive inference may occur locally on the user's wearable or smartphone to reduce latency and preserve privacy, with encrypted model and data updates synchronized periodically. In other embodiments, the raw or partially processed data is sent securely to the learning and modelling server (LMS) 208 for heavier computation—for example, running a complex neural network model—and the results (predictions or alerts) are then sent back to the app.

The LMS 208 is configured to train machine learning and/or AI prediction models to predict menopause related symptoms, based on patient physiological information, and environmental context information. In some embodiments, the predictive models include, for example, but without limitation, a recurrent neural network (RNN), transformer-based temporal sequence model, or an ensemble thereof configured to process multi-modal time-series data and generate individualized risk probabilities. The LMS 208 may be configured to train the prediction models based on the information of a large number of users, to provide more accurate predictions. In various embodiments, the prediction models trained by the LMS 208, may include provisions (such as parameters, arguments, and variables) to incorporate a personalized baseline, to tweak parameters and/or weights of the prediction model, for a personalized symptom prediction, so as to further improve accuracy, and reduce the chances of false positives, and also reduce missed symptom predictions (i.e. false negatives).

In various embodiments, the user device 204 along with the LMS 208 employs a federated learning approach, wherein the LMS 208 trains the prediction models on the LMS 208, without accessing the raw physiological information, and environmental context information of the users. In such embodiments, the LMS 208 receives model updates from the user device 204 (the updates being determined at the user device 204) and incorporates the model updates into an overall prediction model stored at the LMS 208. In other words, the user device 204 accesses a symptom prediction model from the LMS 208, trains the symptom prediction model locally, and share model updates with the LMS 208. In some other embodiments, the LMS 208 may serve as an aggregator of anonymized data from multiple users, received from respective ones of the user devices 204, enabling more advanced model training (as discussed later under privacy-preserving learning). The communication between the user device 204 and the LMS 208 is typically via the internet with encryption (HTTPS, AES, PGP or similar secure channels).

The accuracy of prediction models can improve as more data from many users becomes available, covering a variety of symptom patterns and personal profiles. However, simply uploading all user data to a central server for machine learning poses privacy issues. Embodiments presented herein mitigate this limitation through federated learning and/or on-device processing.

In one implementation, the core predictive model (say a neural network for hot flash prediction) is initially trained on a dataset from clinical studies or early users who consented to data sharing. After deployment, the model resides on each user's device and runs locally. In other words, predictive inference occurs locally on the user's wearable or smartphone to reduce latency and preserve privacy, with encrypted updates synchronized periodically. In some embodiments, the system 300 may classify or monitor users according to established reproductive-aging frameworks such as STRAW-10. The predictive model of the user device 204 may integrate hormonal and menstrual-cycle data to identify transitions between stages or estimate proximity to menopause, refining prediction timing and intervention selection. Further, the predictive model may incorporate demographic and contextual variables including age, ethnicity, ancestry, geographic region, and lifestyle factors to adjust baseline thresholds or symptom probabilities, ensuring accuracy across diverse populations. In some embodiments, the predictive model may incorporate a user profile. The user profile data in turn, may include demographic, genetic, and environmental variables-such as ethnicity, BMI, metabolic status, or prior oncologic or hormonal treatments, that influence symptom manifestation and algorithmic thresholds. Periodically, when the user's device is idle and connected to Wi-Fi (to conserve resources), it will participate in a federated learning round. The app will use its local data (perhaps a cache of recent weeks of sensor data and events) to train the model a bit further, computing updated model weights. Instead of sending raw data to the cloud, it sends only the model weight updates (which are essentially numbers that reflect patterns learned, without revealing the original data). Local model parameters may be aggregated with differential privacy or homomorphic encryption to update a global model without transmitting identifiable raw data. The LMS 208 collects updates from many users, averages them (with techniques to ensure no single user's update is too influential to avoid leakage of personal info), and then sends back the improved model to everyone. In this way, if many users share a similar pattern (for example, a certain HRV drop an hour before a hot flash), the model will learn to recognize that pattern better, benefiting all users, including those who never shared data directly. The system can derive and distribute population-level model improvements across users while preserving individual privacy, thereby enabling cohort-specific predictive models for demographic or hormonal subgroups.

To enhance privacy further, the system can use differential privacy when aggregating updates-adding a small, predefined amount of random noise to each user's model update so that individual quirks are blurred out but the general useful signal remains when averaging many updates. In some embodiments, model updates may be aggregated using a federated-learning protocol in which only gradient parameters not raw sensor or biochemical data are transmitted. Differential privacy ($\varepsilon \leq 1.0$) may be applied to prevent re-identification while maintaining model accuracy. Also, users may be categorized (with their consent) by cohort (e.g., age range, whether they are on hormone therapy or not, etc.) and specialized models can be trained for each cohort, to account for differences in symptom expression, without directly sharing identity or raw data.

All data stored on devices and servers may be encrypted. All data transmissions may be end-to-end encrypted and stored under user-controlled retention policies. Identifiers, model updates, and data exchanges may also be anonymized. For example, if any research is published using this system's data, it will only include aggregate statistics like "average heart rate increase observed 1 minute before hot flashes in the study population" but nothing that can identify individuals.

In various embodiments, predictive performance may be monitored through metrics such as accuracy, sensitivity, specificity, and false-positive rate for ongoing model calibration. The system may also evaluate treatment-response patterns to pharmacologic or nutraceutical therapies, learning which interventions reduce symptoms and optimizing ongoing recommendations. After each intervention, the system scores impact on symptom frequency or intensity and reprioritizes future actions. This adaptive feedback loop improves precision and personalization. Further, clinicians or users may confirm or override predictions, with those confirmations recorded as reinforcement data for continuous model refinement. The result is a continually learning ecosystem. The longer a user is on the system, the more personalized it becomes to her (via her own data and feedback), and the more it benefits from the collective wisdom of the community (via federated learning). Importantly, these benefits are achieved without exploiting personal data inappropriately. The predictive module may also generate a confidence score and a natural-language summary of the physiologic factors contributing to each prediction to enhance model transparency and clinical interpretability. The confidence score may further support clinician interpretability and safety review.

The menopause symptom prediction events predicted by the user device 204 may also be transmitted to the remote patient monitoring server (RPMS) 210. The RPMS 210 may be maintained by or otherwise associated with a healthcare provider (such as a physician's clinic, a hospital, and so forth), or an insurance provider, or both. Clinicians may validate or adjust predicted events through a secure dashboard, and these inputs may be used to refine subsequent model predictions.

As described above, the user device 204 may operate in a clinical mode, wherein the biometric data streams (including physiological and biochemical data), and the environment contextual data streams captured by the sensing devices 202 may be shared with the RPMS 210. In certain embodiments, the system includes or interfaces with a wearable device or home-based monitoring apparatus configured to collect physiological parameters associated with menopausal symptoms. The user device 204 may be configured for continuous or periodic use and may transmit data through network 212 to the RPMS 210.

Such embodiments enable periodic clinical review of the transmitted data, consistent with remote patient monitoring (RPM) requirements, including continuous data collection, transmission frequency thresholds, and physician interpretation workflows. Data can be aggregated for trend analysis and automatic generation of alerts or care recommendations. Clinicians may validate or adjust predicted events through a secure dashboard, and these inputs may be used to refine subsequent model predictions.

As discussed above, the sensing devices 202 and the user devices 204 may be configured to meet regulatory definitions of a medical device for continuous physiological monitoring. The software design of the firmware of the devices may conform to FDA GMLP and medical-device standards (IEC 62304, ISO 14971) to facilitate regulatory compliance. In some embodiments, the devices may implement the Fast Healthcare Interoperability Resources (FHIR) standard, Health Level Seven (HL7) standard or another comparable interoperability standards, to communicate the patient's biometric data streams, and environment contextual data streams, usually in the form of structured data streams. The devices may comply with healthcare privacy and interoperability standards such as HIPAA and FDA 510(k) guidelines and may produce data suitable for medical billing under CPT codes 99453, 99454, 99457, and 99458 or other applicable CPT codes. Such embodiments support transmission of the biometric data stream, contextual data stream, journal inputs predicted symptoms, and actual symptoms, and integration with electronic health records (EHR) and clinician dashboards for real-time intervention and care coordination. Further, the devices may also be configured to maintain audit trails consistent with Software as a Medical Device (SaMD) frameworks and communicate the audit trails with the RPMS 210 as required.

The embodiments described herein are envisioned to be applicable to remote patient monitoring platforms eligible for insurance reimbursement. This involves aspects like data transmission to providers, compliance tracking, and billing integration. In various embodiments, the RPMS 210 is configured to perform all the aforementioned functions, for example, data collection, compliance processing, and integrated billing. All data stored on devices and servers may be encrypted. All data transmissions may be end-to-end encrypted and stored under user-controlled retention policies. Identifiers, model updates, and data exchanges may also be anonymized.

In various embodiments, the user device 204, the LMS 208, and the RPMS 210 may be communicably connected to one another, through a network 212. The network 212 may be any known data communication network, such as, but not limited to, the internet, a cellular network (GSM, CDMA, 2G, 3G, LTE, LTE-A, 5G, or NR), a WLAN, or any combination of such networks. All data transmissions may be end-to-end encrypted and stored under user-controlled retention policies. Any data exchanges may also be anonymized.

Figure 3:
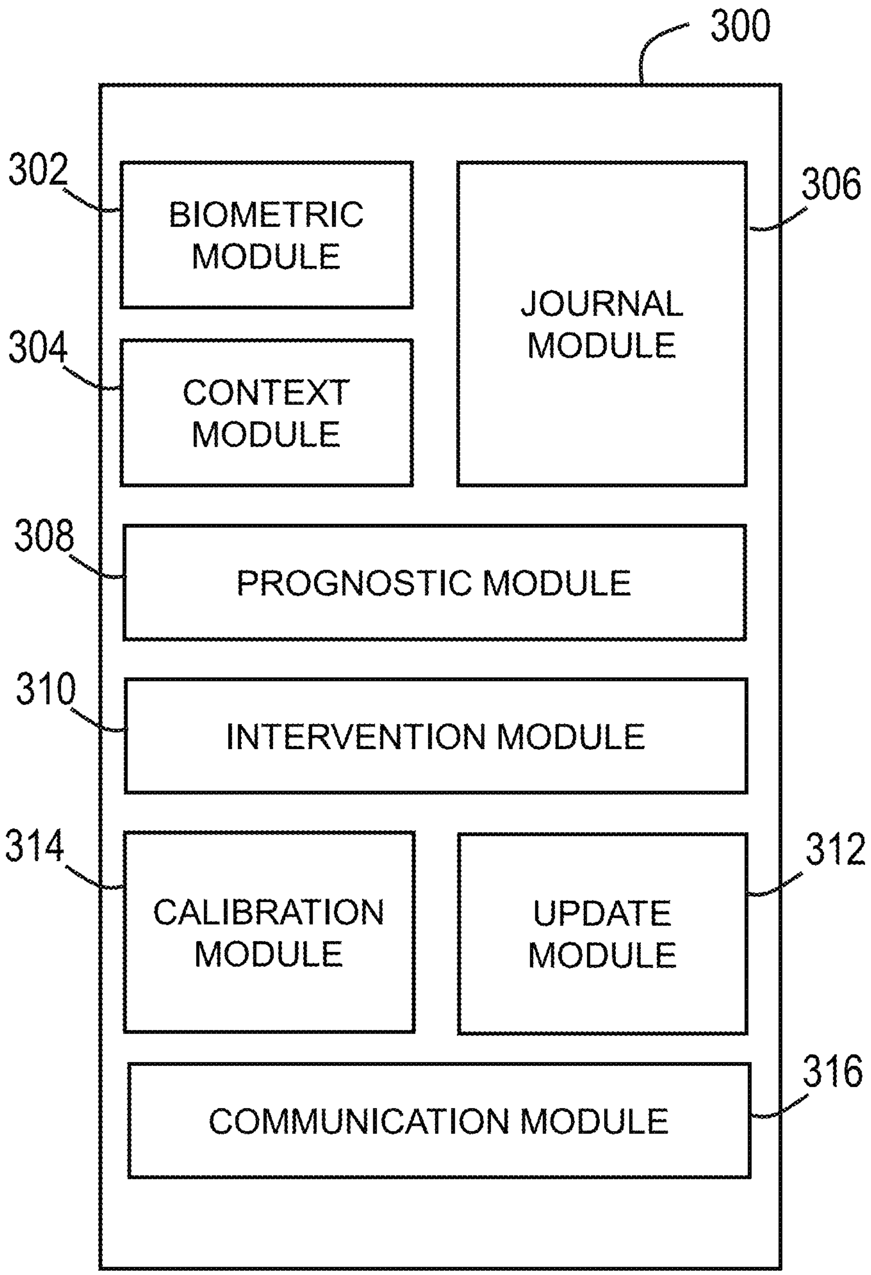
FIG. 3 is a block diagram of an exemplary system for predicting menopause symptoms, according to one embodiment.

FIG. 3 is a block diagram of an exemplary menopause symptom prediction system 300 for predicting menopause symptoms, according to one embodiment. The menopause symptom prediction system 300 includes a biometric module 302, a context module 304, a journal module 306, a prognostic module 308, an intervention module 310, an update module 312, a calibration module 314, and a communication module 316.

The biometric module 302 is configured to receive a plurality of biometric data streams of a user. The biometric streams may include physiological measurements, for example, heart rate variability, body temperature, and blood oxygen saturation. In one embodiment, the biometric module 302 may be configured to receive biochemical measurements including hormonal levels such as, but not limited to, estradiol, progesterone, luteinizing hormone (LH), cortisol, thyroid related biomarkers, follicle-stimulating hormone (FSH), inhibin B, dehydroepiandrosterone (DHEA), and so forth. The biometric module 302 captures the biometric data in the form of one or more time series biometric data streams.

The context module 304 is configured to receive contextual data streams, representing the environment of the user, and physiological state of the user. The environmental information may include, for example, ambient temperature, location of the user in one of several known locations such as the bedroom, the living room, the kitchen, the office, outdoors, and so forth. The physiological state of the user may include, for example, menstrual cycle information of the user, activity level of the user (such as, sedentary, low intensity activity, high intensity activity, walking, running, jogging, playing sport, and so forth), whether the user is standing, sitting, or sleeping, and so forth. The context module 304 captures the context data in the form of one or more time series contextual data streams. The context module 304 may also generate a numerical representation of the context data (for example, a context score). The numerical representation may be, for example, a probability score, a confidence score, an activity score, an ambient condition score, or any combination thereof. The activity score may be assigned based on the activity level of the user—for example, higher activity score for more intense activity, and lower activity score for sedentary or rest. The ambient condition score may be assigned, for example, high for higher ambient temperature (for example, higher than 27° C. or 80° F.), high for the user being located outdoor during mid day, low for lower ambient temperature (for example, less than 20° C. or 68° F.), or low for the user being located indoors at night time, and so forth. It will be appreciated that the ambient condition score may be geographically tailored. The context score may then be aggregated from the activity score, and the ambient condition score, as a probability score or a confidence score. The context score may be representative of the probability or confidence that a menopause related symptom is likely to occur. For example, the context score may be high when the detected activity level is high intensity, and/or the ambient temperature is high, while the probability score may be low when the user is resting or sedentary, and the ambient temperature is low. In some embodiments, the activity score, the ambient condition score, and the context score may range between 0 and 1, or between 0% and 100%.

The journal module 306 is configured to allow the user to input symptom narratives in free text. The journal module 306 may include, for example, a digital journaling application, which accepts free-text input from the user. The user may use the journal application to indicate to the user device 204, what the user feels, prior to, during, or after the occurrence of a menopause related symptom. The journal module 306 may then employ language processing such as natural language processing, machine learning, artificial intelligence, and/or large language models (LLM) to process the user's journal inputs. In some embodiments, the journal application applies natural-language-processing (NLP) algorithms, including tokenization, entity recognition, and sentiment analysis, to convert user-entered free-text symptom narratives into structured, time-stamped data features. In some embodiments, the journal module 306 extracts features such as symptom descriptors, intensity modifiers, temporal references, emotional sentiment, and so forth. The journal module 306 may then encode the extracted features as numerical parameters (such as sentiment scores, intensity scores, and so forth) to be provided to the predictive model. This allows the predictive model to capture symptom patterns and triggers that may not be apparent from the user's biometric signals alone.

The journal module 306 may thus accept user reported symptoms, and/or periodic or aperiodic user logs or surveys about the user's quality of life including, for example, the user's mood, sleep quality, aches and pains, and so forth. In some embodiments, the journal inputs may also include self-reported depression or environmental stressors detected via passive audio or questionnaire inputs, that may be indicators for mood, stress, or safety. The journal module 306 may then utilize language processing (as described above), to extract and log information about the symptoms, such as, but not limited to, severity of the symptoms, typical timing of the symptoms, frequency of occurrence of the symptoms, trends of occurrence of the symptoms, and so forth. In some embodiments, the journal module 306 may also identify Current Procedural Terminology (CPT) codes associated with the interventions suggested or effected for the user, for the predicted menopause related symptom. Such CPT codes may be useful for healthcare professionals to track patient care, and for insurance providers to enable quicker disbursements or reimbursements for the care provided to the user.

In some embodiments, the journal module 306 may also capture, allow user inputs, or input from other sources (such as testing laboratories, healthcare providers, clinics, hospitals, and so forth), for entering further biometric, or contextual information otherwise not captured by sensors or sensing devices 202. Such parameters include behavioral and environmental factors (stress, caffeine, alcohol, medication timing, exercise, ambient heat or light), psychosocial and behavioral context data (which may identify chronic stress, mood disturbance, or environmental instability influencing symptom expression). These may be captured via self-report, passive data, or validated screening tools, enabling adaptive recommendations or clinician referral. Such inputs may be integrated to improve personalized prediction and guide preventive interventions.

The prognostic module 308 is configured to predict the menopause symptoms of the user, before the symptom occurs, or at the onset of the occurrence of the symptom. The prognostic module 308 may use the biometric information received from the biometric module 302, and the context information received from the context module 304. The prognostic module 308 may also utilize journal inputs received from the user. In some embodiments, predictions may rely solely on contextual data streams and/or journaling data when continuous biometric data streams are unavailable.

The prognostic module 308 may access a personalized biometric baseline, wherein the personalized biometric baseline is previously established based on the plurality of biometric data streams. In various embodiments, the personalized biometric baseline may be established in the calibration mode, by the prognostic module 308. The prognostic module 308 may learn a normal biometric baseline, indicating the biometric data (such as heart rate, skin temperature, skin conductance, biochemical markers, and so forth), and variance thereof, recorded when the user is not experiencing a hot flash. The prognostic module 308 may then generate a personalized biometric baseline, by modifying the learnt normal biometric baseline, with numerical representations of the context data streams (or context score), including, but not limited to, activity scores representing the user's activity levels (whether resting/sedentary, light activity, moderate activity, or intense activity), ambient condition scores representing the ambient temperature and/or location of the user (for example, indoors, outdoors, in commute), and so forth. The prognostic module 308 then modifies the learnt normal biometric baseline, based on the numerical representations of the context data streams (or context score), to obtain the personalized biometric baseline. In some embodiments, "modifying" the normal biometric baseline includes scaling the normal biometric baseline based on the numerical representation of the context data streams. In some other embodiments, "modifying" the normal biometric baseline includes applying a probability score to the normal biometric baseline, based on the numerical representation of the context data streams. The probability score is representative of the likelihood of experiencing a menopause related symptom, in the user context identified by the context data streams. For example, the user may have a higher probability of experiencing hot flashes during intense activity levels, elevated ambient temperatures, and being outdoors in direct sunlight.

In the calibration mode, when the user experiences a hot flash, the user may enter a journal entry indicating that she has experienced or is currently experiencing a hot flash, the severity of the hot flash, and the subjective feeling she experienced during the hot flash—for instance, particular discomfort. Such occurrences are marked by the prognostic module 308 as a hot flash event. The prognostic module 308 may mark such occurrences as time stamps in the biometric data streams, including the indicated time window of the occurrence of the hot flash, as indicated by the user. The prognostic module 308 may also mark the context data streams with the same time stamps, to correlate the context data streams with the biometric data streams during the hot flash event. The prognostic module 308 may then learn the patterns of the biometric data streams corresponding to the user indicated hot flash event and record them as menopause symptom biometric data.

Thus, the prognostic module 308 learns the personalized biometric baseline, and the biometric patterns associated with the occurrence of the menopause related symptom, within the user context indicated by the context data streams. Further, the prognostic module 308 may also associate the learned biometric patterns associated with the occurrence of the menopause related symptom, with the user's subjective experience as indicated in the journal entries, and the numerical parameters of the language features extracted from the journal entries.

At the end of the calibration mode, the prognostic module 308 switches to operating in the prognostic mode, where the prognostic module 308 may then utilize the personalized biometric baseline, the learned biometric patterns associated with the occurrence of the menopause related symptoms, the user context information (including the context score, the activity score, the ambient condition score), and the user's subjective experience derived from the user's journal entries (for example, using the numerical parameters of the language features extracted from the journal entries), to predict the menopause related symptoms before they occur.

Based on the personalized biometric baseline, the biometric information, and the context information, the prognostic module 308 monitors the plurality of biometric data streams and contextual data streams for deviations from the personalized biometric baseline. The deviation may be determined based on absolute values of the data streams from the personalized biometric baseline. Alternatively, the deviation may be determined based on the rate of change of the data in the data streams observed over a predefined time window. In some embodiments, the deviation may be determined based on the absolute values of the data streams, and the rate of change of the data in the data streams within the predefined time window. In some other embodiments, the prognostic module 308 may dynamically adjust whether to use the absolute values, or time rate of change of data, or both metrics, to determine the deviation from the personalized biometric baseline. In various embodiments, the prognostic module 308 may detect deviations in a continuous manner, comparing each value of the received biometric data stream with a corresponding value within the personalized biometric baseline. In alternate embodiments, the prognostic module 308 may detect deviations using a moving window, comparing a set of contiguous values of the received biometric data stream, with a corresponding set of contiguous values within the personalized biometric baseline.

The prognostic module 308 may then detect, using a predictive model, a pattern of physiological deviation from the personalized biometric baseline and correlating with an impending menopause-related symptom.

In some embodiments, the predictive models include, for example, but without limitation, a recurrent neural network (RNN), Long Short-Term Memory (LSTM) models, transformer-based temporal sequence model, or an ensemble thereof configured to process the multi-modal time-series data (in other words, the plurality of the biometric data streams, and/or the context data streams) and generate individualized risk probabilities of a menopause related symptom occurring. Based on the detected pattern, the prognostic module 308 may predict, based on detecting the pattern of physiological deviation, an occurrence of the menopause-related symptom before or as it begins.

In some embodiments, the prognostic module 308 may detect a pattern of deviation of the biometric data from the personalized baseline, over a prediction time window. The prediction time window may be of a preset duration, or may be of a dynamically or adaptively configured duration, based on the parameters of the predictive model, for example, the RNN model. The RNN is an artificial neural network particularly suited to processing sequential data, such as the time series of biometric data, by logging the current biometric data stream values in a memory and utilizing current and past biometric data stream values to make predictions of future biometric values for the user. Thus, changes in the biometric data (including the physiological data of the user, and the biochemical data of the user) over the prediction time window, are used to estimate particular ones of biometric parameters of the user—for example, heart rate, and skin temperature, elevations of which are indicative of an menopause related symptom. RNNs are particularly useful for shorter prediction time windows, for example, 1-2 minutes, wherein the number of data points in the biometric stream are limited to, for example, 100 data points.

In alternative embodiments, the prognostic module 308 may employ LSTM, which is a form of an RNN, with a larger prediction time window. LSTM is also better suited to avoid the vanishing gradient problem of RNNs. A vanishing gradient occurs during updating weights of a RNN, when gradients diminish as they propagate backwards during training the RNN. With diminishing gradients, weights of a layer are updated minimally or not at all during training the RNN, thus leading to sub-optimal or incorrect pattern detection and thus incorrect predictions of the menopause related symptom. LSTMs may have a longer prediction time window, for example, 10-15 minutes, wherein the number of data points in the biometric stream can approach several hundred to a thousand data points.

In still other embodiments, the prognostic module 308 may employ both-LSTMs for detecting a much smaller time frame within which an impending menopause related symptom may occur, and switch to an RNN to accurately predict the impending menopause related symptom, and it's severity.

The prognostic module 308 may then compare the predicted biometric parameters, to the personalized biometric baseline, to identify the patterns of deviation from the personalized biometric baseline. The prognostic module 308 may utilize an adaptive, or dynamic threshold to identify patterns of deviation that may relate to an impending menopause related symptom. The prognostic module 308 may dynamically or adaptively determine the threshold, based on the user context—for example, user's activity levels (whether resting/sedentary, light activity, moderate activity, or intense activity), ambient temperature, location of the user (for example, indoors, outdoors, in commute), the aggregate context score, and so forth. For example, the threshold may be lower during moderate activity, or intense activity, or high ambient temperature, making the model more sensitive to deviations from the personalized biometric baseline, when the user is performing intense activity or is outdoors, for example. Conversely, the threshold may be higher during rest or sedentary periods, or low ambient temperature, making the model less sensitive to deviations from the personalized biometric baseline when the user is comfortably resting at home, for example.

In various embodiments, the prognostic module 308 computes a probability of occurrence of the menopause related symptom, in the prediction time window, based on the deviation from the personalized baseline. The prognostic module 308 may compute the similarity score, based on the pattern of physiological deviation being similar to a known physiological deviation associated with a historical menopause related symptom event. In other words, if the pattern of deviation from the personalized baseline, up to that instance in the prediction time window closely matches the pattern of deviation associated with a known historical menopause related symptom event, the prognostic module 308 increases a similarity score of the menopause related symptom occurring. The prognostic module 308 may compute the similarity score continuously or at preset intervals. The prognostic module 308 may predict the menopause related symptom, based on the similarity score crossing a preset threshold (for example, 90% probability). The duration between the similarity crossing the preset threshold, and the predicted instance of occurrence of the menopause related symptom, is defined as the prediction horizon. In other words, the prediction horizon is a lead time before the onset of the menopause related symptom, when the system 300 determines that the probability of the menopause related symptom occurring in the future, crosses a preset threshold.

The prognostic module 308 may then transmit a signal to the intervention module 310, upon a prediction of an impending menopause symptom. In some embodiments, the system 300 may classify or monitor users according to established reproductive-aging frameworks such as STRAW-10. The predictive model of the prognostic module 308 may integrate hormonal and menstrual-cycle data to identify transitions between stages or estimate proximity to menopause, refining prediction timing and intervention selection. Thus, the prognostic module 308 identifies early markers of impending symptoms and proactively provides recommendations or initiates interventions to prevent the symptom from fully manifesting. For example, upon detecting a precursor pattern associated with a hot flash, the system may prompt the user to hydrate, perform a brief guided-breathing exercise, or automatically adjust ambient temperature. This preventive capability transforms the system from a passive alert tool into an active therapeutic engine that limits symptom intensity or occurrence. The predictive module may also generate a confidence score and a natural-language summary of the physiological factors contributing to each prediction to enhance model transparency and clinical interpretability. The confidence score may further support clinician interpretability and safety review.

In one embodiment, the prognostic module 308 may correlate the derived information of the user's symptoms from user's journal entries, with the user's biometric data, and the user's context information, to improve the accuracy of prediction of the menopause related symptoms. The extracted linguistic features, such as emotional tone, symptom intensity keywords, and temporal references, are numerically encoded and correlated with biometric and contextual data. The user device 204 dynamically recalibrates prediction thresholds of the prediction model, based on sentiment-weighted symptom intensity, thereby refining model sensitivity to the user's subjective experience. Thus, the prognostic module 308 employs a multi-modal approach to predict the menopause related symptoms to enhance accuracy of the system 300.

In one embodiment, the prognostic module 308 correlates biochemical measurements with the physiological information and the user's contextual data to enhance accuracy of symptom prediction and to identify pre-symptomatic hormonal fluctuations predictive of upcoming menopause-related events. In another embodiment, the user device 204 may further correlate the physiological information and the environmental contextual information with HRT regiment adherence and response over time, to generate predictions of therapeutic efficacy or recommend timing adjustments, and improve prediction accuracy.

In some embodiments, the prognostic module 308 includes an explainability module configured to calculate feature-importance rankings for each prediction, thereby identifying key physiological, biochemical and contextual contributors to the predicted symptom. The prognostic module 308 may provide explainability outputs identifying which physiological or contextual variables most influenced a prediction, improving clinical transparency. The prognostic module 308 may further include a traceability module that records feature contributions and confidence scores for each prediction and maintains an interpretable event log accessible to clinicians or users for transparency, compliance, and model retraining. The explainability module and confidence score may further support clinician interpretability and safety review.

It should be noted that the system 300 and prognostic module 308 are configured to predict the menopause related symptom before it occurs, rather than simply detecting the menopause related system as it occurs. Some events like hot flashes can be detected as they start (with minimal or very short advance warning) by thresholding. In some embodiments, the system 300 may do this as a backup for any missed predictions. However, system 300 and prognostic module 308 are particularly configured for early prediction (before the user would normally notice the symptom). In practice, a combination of immediate detection and short-term prediction yields the best user experience: immediate detection ensures no event goes completely unnoticed by the system, and prediction gives a warning just beforehand when possible. For example, the system might detect the onset of a hot flash and simultaneously note that its prediction module had a high score 1 minute earlier, reinforcing that the model is on track and could potentially push that alert slightly earlier next time or with high confidence. The predictive algorithms of the prognostic module 308 may be configured to identify physiological or biochemical precursors of menopause-related symptoms a pre-set duration prior to the expected onset of the symptom (for example, 5 minutes prior, 10 minutes prior, and so forth), depending on the user's calibration profile and data quality. Such early-detection thresholds may be dynamically extended (for example, 15 minutes prior, 25 minutes prior, and so forth) as the model gains confidence, allowing sufficient lead time for preventive or mitigating actions. The durations indicated herein are purely exemplary, and any other early-detection threshold durations may be employed.

In some embodiments, the prognostic module 308 may also determine a counterfactual simulation, which modifies selected contextual variables (e.g., ambient temperature, caffeine intake, sleep duration) to recompute symptom intensity scores under alternative conditions. The resulting comparative probabilities are then transferred to the intervention module 310, to present to the user as 'what-if' insights, quantifying how behavioral or environmental changes may reduce the predicted symptom risk.

The intervention module 310 is configured to, responsive to the predicting, initiate an intervention action. The intervention action comprises at least one of: presenting to the user a notification of the predicted menopause-related symptom, transmitting a control signal to an external device to mitigate the menopause-related symptom, and presenting a recommendation to the user to perform a mitigating activity. Intervention actions include but are not limited to environmental adjustments (temperature, airflow, lighting), wearable actuation, micro-vibration feedback, biofeedback cues, medication prompts, and behavioral coaching. In various embodiments, intervention actions also include one or more of pharmacologic, nutraceutical, or digital-therapeutic interventions. The intervention module 310 may transmit a control signal to the appropriate intervention device 206, based on the selected intervention action.

In various embodiments, the intervention module 310 is configured to select among a plurality of candidate intervention actions. The intervention module 310 may select the intervention action, which may result in the largest suppression of the predicted symptom intensity. The intervention module 310 receives the predicted symptom intensity score for the predicted symptom from the prognostic module 306 and accesses historical symptom intensity scores from the update module 312. The intervention module 310 then selects the most appropriate intervention action that may result in the largest suppression of the predicted symptom intensity, based on a comparative evaluation of the predicted symptom intensity score, and the historical symptom intensity scores.

In various embodiments, the system 300 may also include an update module 312. The update module 312 is configured to update at least one of the personalized biometric baseline, and the predictive model, based on at least one of the plurality of biometric data streams, the detected pattern of physiological deviation, the predicted menopause related symptom, a user feedback pertaining to the predicted menopause related symptom, and the user's journal inputs. The update module 312 may also be configured to store timestamps, biometric data, and contextual data, for every predicted symptom, the predicted symptom intensity, occurrence of the actual symptom, and the actual symptom intensity. The update module 312 may also be configured to store the intervention action recommended by the intervention module 310, for each predicted symptom. Thus, the update module 312 may store the symptoms and interventions in a tabular form, or data vectors, which include, for each symptom episode, timestamps, biometric data, and contextual data, the predicted symptom intensity, the intervention action, and the actual symptom intensity. Such a storage of all occurrences of the symptoms allows for selection of appropriate intervention actions that may result in the largest suppression of symptom intensity (as determined by the variance between the predicted symptom intensity and the actual symptom intensity), and thus effect continual improvement of intervention action suggestions, extension of a lead-time for the symptom prediction and intervention action suggestions, or both. The predictive model may include a personalization loop wherein model parameters may be dynamically adjusted based on longitudinal (i.e. time series) user data, thus improving predictive accuracy and intervention timing over time.

Each user's model instance continuously recalibrates prediction parameters based on user-specific physiological baselines and counterfactual outcomes. Model retraining may occur locally (on-device) or through federated learning, employing differential privacy with calibrated Gaussian noise (ε≤1.0, 0≤10-5) and secure averaging to prevent reconstruction of individual data. In some embodiments, model updates may be aggregated using a federated-learning protocol in which only gradient parameters—not raw sensor or biochemical data—are transmitted. Differential privacy (ε≤1.0) may be applied to prevent re-identification while maintaining model accuracy. The adaptive model supports predictive time windows (5-60 minutes) and configurable intervention thresholds based on user confidence and physiological signal reliability.

In some embodiments, the update module 312 evaluates the intervention actions that may reduce the likelihood or severity of that symptom before it occurs. The update module 312 analyzes prior episodes and corresponding user behaviors such as hydration, caffeine intake, sleep duration; ambient conditions; and interventions administered, to identify modifiable factors associated with symptom onset. Based on this analysis, the update module 312 updates and/or configures the predictive models to recommend appropriate pre-emptive interventions, including hydration reminders, guided breathing, temperature adjustment, or activity modifications, that have been statistically correlated with reduced symptom probability. The update module 312 thus enables the predictive model to function as an adaptive prevention engine that continuously learns from prior events to lower recurrence risk, not merely to notify the user. The update module 312 may further evaluate the effectiveness of prior interventions and prioritize those that historically reduce event severity, based on feedback received from the user, the user's journal inputs, and the measured biometric data. In some embodiments, clinicians or users may confirm or override predictions, with those confirmations recorded as reinforcement data for continuous model refinement. Hormone-level inputs (e.g., estradiol or cortisol values from wearable or periodic biosensors) can refine these predictions and personalize preventive guidance. Behavioral cues, such as prompting the user to drink something cool or rest in a ventilated area may be automatically delivered through the companion application.

In various embodiments, predictive performance may be monitored through metrics such as accuracy, sensitivity, specificity, and false-positive rate for ongoing model calibration. The update module 312 may also evaluate treatment-response patterns to pharmacologic or nutraceutical therapies, learning which interventions reduce symptoms and optimizing ongoing recommendations. After each intervention, the update module 312 scores impact on symptom frequency or intensity and reprioritizes future actions. This adaptive feedback loop improves precision and personalization. The result is a continually learning ecosystem.

In various embodiments, the system 300 may also include a calibration module 314. The calibration module 314 is configured to establish the personalized biometric baseline in a calibration mode, wherein the calibration mode spans at least two days of data collection during which no menopause related symptoms are detected and configure the predictive model with the user's baseline circadian patterns and filtering out routine activities to reduce false positive predictions. In some embodiments, the system 300 may classify or monitor users according to established reproductive-aging frameworks such as STRAW-10. The predictive model of the prognostic module 308 may integrate hormonal and menstrual-cycle data to identify transitions between stages or estimate proximity to menopause, refining prediction timing and intervention selection.

The communication module 316 is configured to communicate with the LMS 208 and the RPMS 210. The communication module 316 may communicate model updates, anonymized user information, and information extracted from the user's journal inputs to the LMS 208, to improve the predictive models. In some embodiments, the communication module 316 may encrypt the information before transmitting it to the LMS 208. In some embodiments employing federated learning, local model parameters may be aggregated with differential privacy or homomorphic encryption to update a global model without transmitting identifiable raw data. In some embodiments, model updates may be aggregated using a federated-learning protocol in which only gradient parameters—not raw sensor or biochemical data—are transmitted. Differential privacy ($\varepsilon \leq 1.0$) may be applied to prevent re-identification while maintaining model accuracy.

The communication module 316 may also communicate the user's biometric information, the user's journal inputs, the information extracted from the user's journal inputs, and identified CPT codes to the RPMS 210. The communication module 316 may communicate with the RPMS 210 for a clinical remote patient monitoring implementation, where a patient's (i.e. the user's) information is required to support clinical logging, and insurance payouts. The communication module 316 may encrypt the information before transmitting it to the RPMS 316.

The system 300 thus provides a specific improvement to the functioning of computer-implemented health monitoring systems. Instead of applying fixed thresholds to raw sensor data, the system uses a personalized baseline model, multi-modal sensor data fusion including the user's biometric data, user's context information, and the user's subjective feelings and/or experience (through the journal inputs), and a prediction engine configured to detect precursor patterns of menopause-related symptoms before onset. By dynamically adjusting decision thresholds based on the user's learned biometric (physiological and/or biochemical) information, and user's context (activity, environment, location), and by automatically triggering device-level interventions without manual rule authoring, the system reduces false positives, reduces unnecessary alerts, and improves the stability and accuracy of symptom prediction compared to conventional rule-based monitoring systems.

Figure 4:
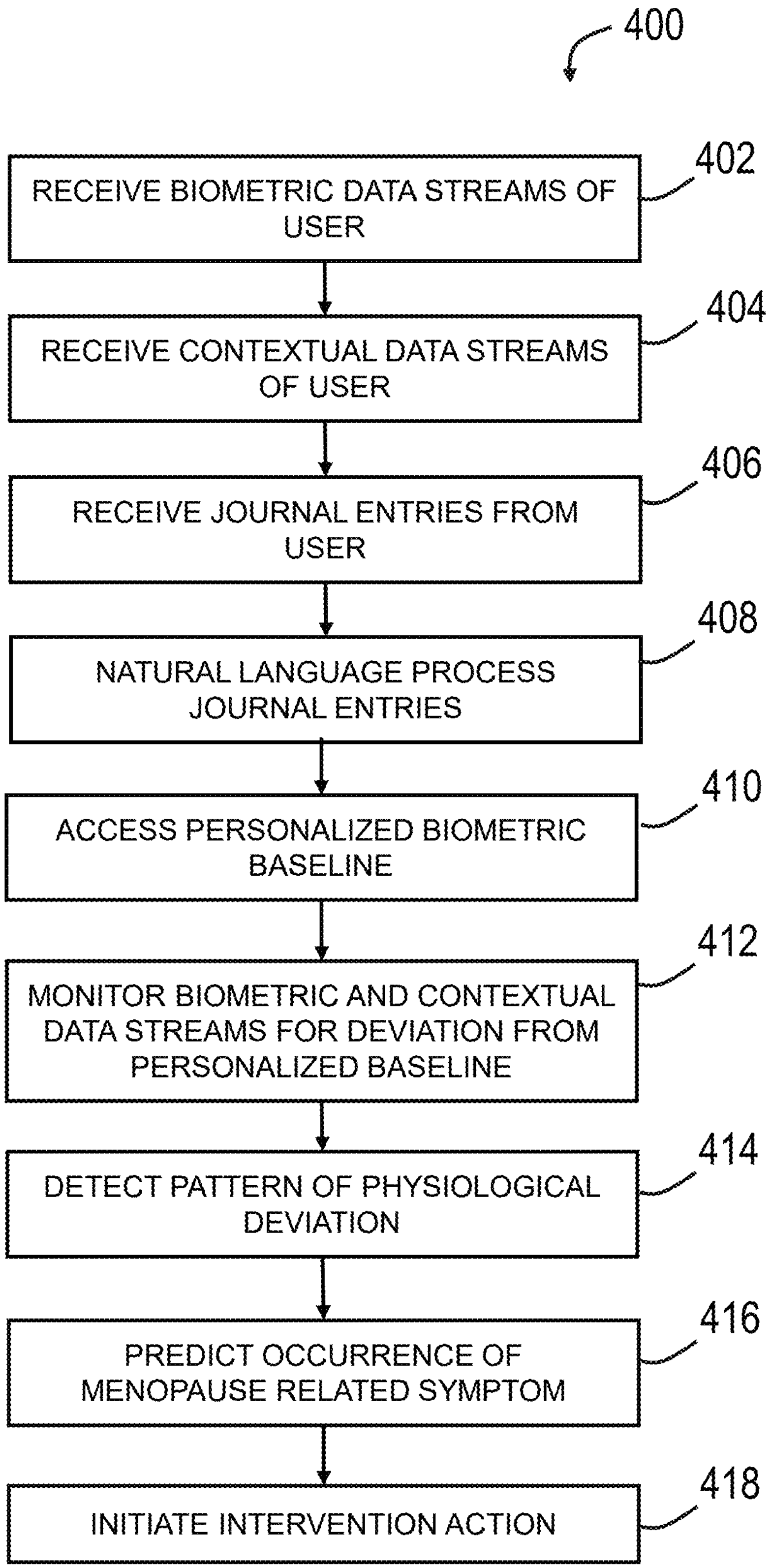
FIG. 4 is a flowchart illustrating an example method of predicting menopause symptoms, according to one embodiment.

FIG. 4 is a flowchart illustrating an example method 400 of predicting menopause symptoms, according to one embodiment At step 402, the system 300 receives a plurality of biometric data streams of a user, including at least heart rate, heart rate variability, body temperature, and blood oxygen saturation. The biometric data streams may be collected in real time, at pre-set intervals. The system 300 may preprocess the biometric data stream, for example, smoothing or filtering noise from the sensors (for instance, removing motion artifacts from the PPG signal to get accurate HR/HRV). The system 300 may also compute derived metrics as features, such as the short-term HRV index, rate of change of skin temperature, sweating rate if EDA or another proxy is available, or combining accelerometer data to detect if the user is awake or asleep.

At step 404, the system 300 receives contextual data streams, including ambient temperature, and menstrual cycle information of the user. The system 300 may receive the contextual data streams of environmental information, such as current ambient temperature or humidity, for example, from the phone's sensors or a nearby smart home sensor, or weather API using location data. The system 300 may aggregate the contextual data streams of environmental information for the current time window, (for example, the last minute or last 5 minutes of data) into a feature vector or a time-series window. The system 300 may also compute the activity score, the ambient condition score, and the aggregate context score, at this step.

At step 406, the system 300 receives the user's journal entries. The journal entries include free text inputs from the user describing her subjective experiences during previous menopause symptom episodes. The journal entries describe, for example, the user's feelings, and/or environmental context, which may otherwise not be captured from the biometric data streams and/or the contextual data streams.

At step 408, the system 300 natural language processes the user's journal entries, to identify natural language features. The natural language features may include, for example, emotional tone, symptom-intensity descriptors, and temporal references. In some embodiments, the system 300 may also numerically encode the natural language features, for example, as a score, a probability metric, or the like.

At step 410, the system 300 accesses a personalized biometric baseline, wherein the personalized biometric baseline is previously established based on the plurality of biometric data streams. The personalized biometric baseline is previously established based on a method described in conjunction with FIG. 5 below.

At step 412, the system 300 monitors the plurality of biometric data streams and contextual data streams for deviations from the personalized biometric baseline. In various embodiments, the system 300 may detect deviations in a continuous manner, comparing each value of the received biometric data stream with a corresponding value within the personalized biometric baseline. In alternate embodiments, the system 300 may detect deviations using a moving window, comparing a set of contiguous values of the received biometric data stream, with a corresponding set of contiguous values within the personalized biometric baseline.

At step 414, the system 300 detects, using a predictive model, a pattern of deviation from the personalized biometric baseline and correlating with an impending menopause-related symptom. In various embodiments, the system 300 may employ the computed activity score, ambient condition score, aggregate context score, and the sentiment score, to detect the pattern of deviation. For example, the system 300 may adaptively set thresholds in the predictive model, based on the activity score, the ambient condition score, the aggregate context score, the sentiment score, or any combination thereof.

The method 400 may utilize one or more predictive models. In one embodiment, a binary classifier model is used for each type of symptom (e.g., a "hot flash predictor" model, a "night sweat predictor", a "mood swing predictor", etc.), each outputting a likelihood or risk score. In another embodiment, a single multi-output model looks at patterns and can label the type of symptom likely to occur. The model can be a machine learning classifier trained on a large dataset of labeled episodes from many users (with privacy measures as described later). For example, a deep neural network might take as input the last N minutes of biometric data (where N could be, say, 10 minutes or an hour, depending on the symptom), predict a future value of the biometric data, compare the predicted future value to the personalized biometric baseline, and detect a pattern of deviation of the predicted future value from the personalized biometric baseline, subject to one or more thresholds set within the predictive model. In some embodiments, the system 300 may classify or monitor users according to established reproductive-aging frameworks such as STRAW-10. The predictive model of the prognostic module 308 may integrate hormonal and menstrual-cycle data to identify transitions between stages or estimate proximity to menopause, refining prediction timing and intervention selection. Further, the predictive model may incorporate demographic and contextual variables including age, ethnicity, ancestry, geographic region, and lifestyle factors to adjust baseline thresholds or symptom probabilities, ensuring accuracy across diverse populations. In some embodiments, the predictive model may incorporate a user profile. The user profile data in turn, may include demographic, genetic, and environmental variables such as ethnicity, BMI, metabolic status, or prior oncologic or hormonal treatments, that influence symptom manifestation and algorithmic thresholds.

At step 416, the system 300 predicts, based on detecting the pattern of biometric deviation, and the natural language features identified from the journal inputs, an occurrence of the menopause-related symptom, a prediction horizon before the menopause-related symptom begins. The prediction horizon is defined as the duration in the prediction time window between the instance at which the probability of a predicted menopause related symptom occurring crosses a preset threshold, and the onset of the predicted menopause related symptom. In other words, the prediction horizon is a lead time before the onset of the menopause related symptom, when the system 300 determines that the probability of the menopause related symptom occurring in the future, crosses a preset threshold.

The system 300 may compute the probability score of occurrence of a future menopause related symptom, based on the pattern of physiological deviation being similar to a known physiological deviation associated with a historical menopause related symptom event. The prognostic module 308 may compute the probability score continuously or at preset intervals.

The method 400 may be configured to detect patterns such as a steady rise in peripheral temperature combined with certain heart rate fluctuations that typically precede the user's self-reported hot flashes during training data. An example rule or learned pattern might be: "If skin temperature is rising faster than 0.2° C. per minute and heart rate is concurrently elevating by more than 5 BPM in that minute, while the user is inactive (no large movement) and ambient temperature is constant, then probability of a hot flash in next 2 minutes is high." The machine learning model would encode such relationships in a more complex, non-linear way, allowing combinations of features and time lags. It might also incorporate longer-term trends; for instance, noticing that over the past week, the user's average nighttime HRV has been dropping, which could correlate with an overall increase in sympathetic activation typical of perimenopause progression-thus increasing sensitivity to detecting any small hot flash signals.

For sleep disturbance predictions, the method 400 may be configured to use prior sleep quality metrics plus current signals (like sweating or minor temperature rises at night) to predict an awakening or a hot flash during sleep. For mood or cognitive symptoms (like an impending anxiety episode or "brain fog"), physiological proxies such as elevated resting heart rate, poor sleep from previous nights, and hormonal cycle stage may be factored in by the model.

At step 418, the system 300, responsive to the predicting, initiates an intervention action, wherein the intervention action comprises at least one of: presenting to the user a notification of the predicted menopause-related symptom, transmitting a control signal to an external device to mitigate the menopause-related symptom, and presenting a recommendation to the user to perform a mitigating activity. The interventions may include environmental adjustments (temperature, airflow, lighting), wearable cooling or vibration actuation, medication or hydration prompts, or behavioral guidance notifications. Intervention actions include but are not limited to environmental adjustments (temperature, airflow, lighting), wearable actuation, micro-vibration feedback, biofeedback cues, medication prompts, and behavioral coaching. In various embodiments, intervention actions also include one or more of pharmacologic, nutraceutical, or digital-therapeutic interventions. Actuation commands may be issued through Bluetooth, Wi-Fi, or cloud APIs to connected systems such as thermostats, fans, or smart bedding. Further, each intervention may be tagged with a contextual confidence score and logged for longitudinal learning and model retraining.

When the method 400 indicates a symptom is likely or beginning, the system 300 may transition to the response phase. The system 300 may generate an alert through the user device 204. Exemplary alerts may be a smartphone push notification, a vibration or tone on the wearable itself, or even a voice alert via a connected speaker. The alert message may say, for example: "Early Alert: You may experience a hot flash shortly. Taking action now." The alert can include a brief explanation or insight (the system might present a note like "Your heart rate and temperature rose above your normal range"). Providing such insight helps the user trust and understand the system 300 predictions.

In some embodiments, the method 400 may simultaneously initiate one or more interventions via intervention devices 206 or app-guided actions. If the user owns a smart cooling wearable (like a cooling bracelet or necklace), the system sends a command to that device to begin a cooling cycle to preempt or lessen the hot flash's intensity. These wearables often use Peltier elements to create a cool sensation on the skin, which can provide relief from hot flashes. Activating it early could shorten the hot flash or reduce discomfort. If integrated with home automation, the system can lower the thermostat or turn on a fan in the room. If it's nighttime, it could also slightly adjust bedding conditions (assuming integration with a smart bed cooling system, for example). The smartphone app could display a quick breathing exercise prompt ("Tap to begin a 2-minute cooling breath exercise"). Breathing techniques or mindfulness can help reduce anxiety or manage sudden heat sensations. For mood-related predictions (if the system expands to that), an intervention might be to play calming music or issue a nudge like "It seems you might be feeling anxious; how about a short walk or a few deep breaths?". The interventions can be personalized and chosen by the user in settings. Some users may prefer only notifications and handle things themselves; others might enable full automation for certain devices.

In some embodiments, the system executes a closed-loop control sequence comprising (1) prediction of an impending vasomotor or sleep-disruptive event, (2) determination of a suitable pre-emptive intervention based on confidence thresholds and user preferences, and (3) automated or semi-automated actuation of one or more devices or prompts. Such a closed-loop implementation of system 300 as described here, senses a physiological event, decides on an action, performs the action, and may even verify the effect. For instance, after turning on a cooling device, the system will observe the user's skin temperature and heart rate. Ideally, it will see the temperature stabilize or drop and heart rate come down within a few minutes, confirming that the intervention helped. That result can be recorded (if the intervention did not achieve the desired effect, the system might try a different or additional measure next time, or mark that event for review). In scenarios where an alert is given but the user is driving or in a situation where an automated action (like cooling) might not be available, the system 300 may schedule the intervention for when possible or just store the prediction.

Figure 5:
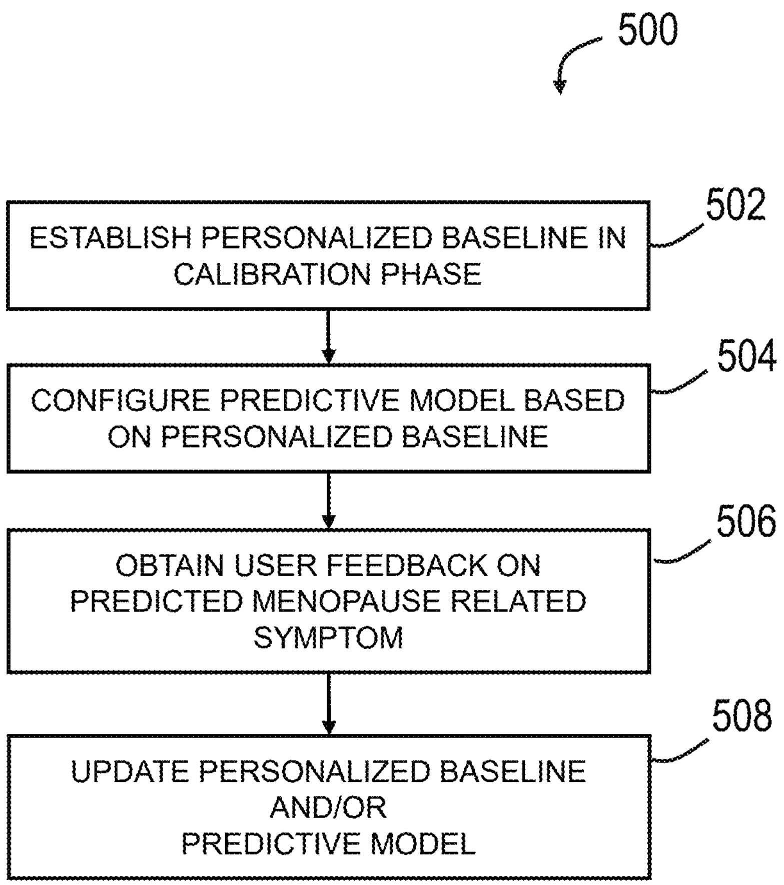
FIG. 5 is a flowchart illustrating an example method of establishing and updating a personalized biometric baseline, according to one embodiment.
Figure 6:
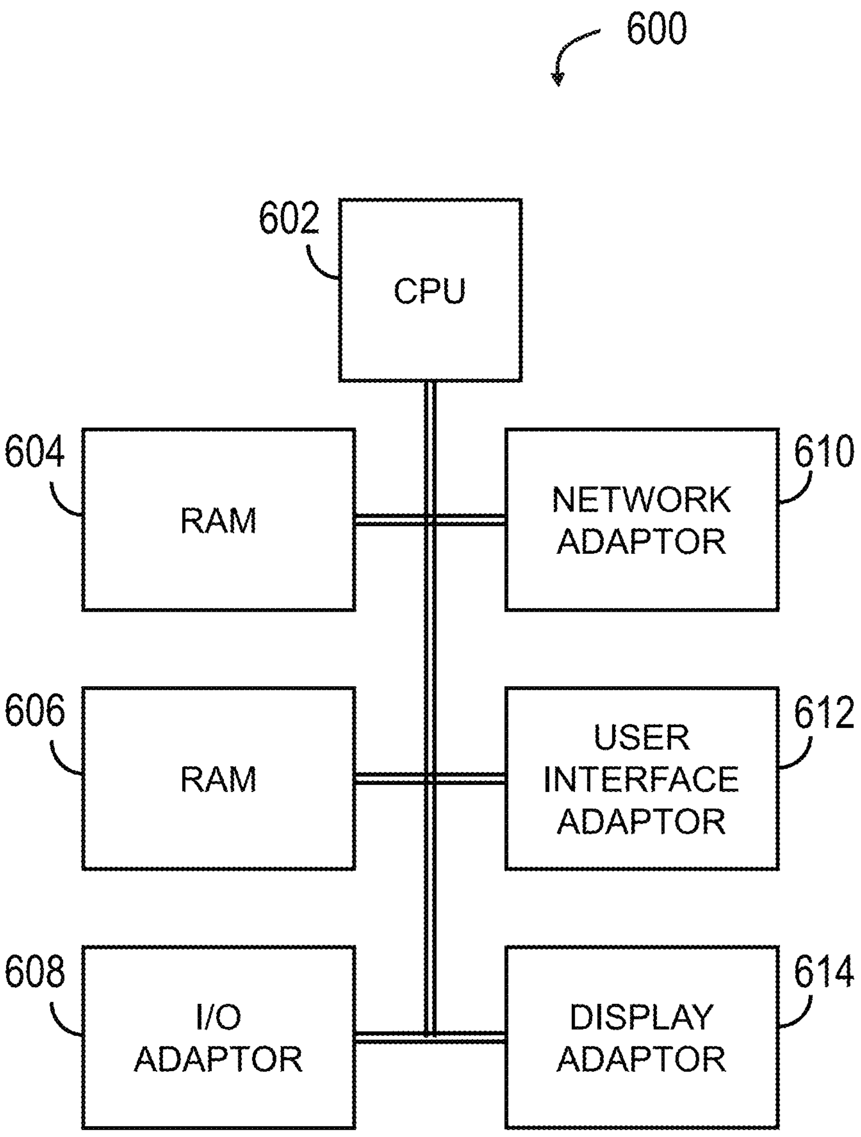
FIG. 6 illustrates a general-purpose computing system for implementing various modules of a menopause symptom prediction system, according to one exemplary embodiment.

FIG. 5 is a flowchart illustrating an example method 500 of establishing and updating a personalized biometric baseline, according to various embodiments.

At step 502 the system 300 establishes the personalized biometric baseline in a calibration mode, wherein the calibration mode spans at least two days of data collection during which no menopause related symptoms are detected.

In various embodiments, the method 500 may be implemented when a user first starts using the system, i.e. in a calibration mode, for example. During an initial period (which could be configurable, for example but not limited to, the first two weeks of consistent use), the system 300 operates to learn the user's baseline physiological patterns and establishing initial thresholds for physiological information. During the calibration mode, the system may also prompt the user to log any menopause-related symptoms they experience, to help label the data (e.g., pressing a button in the app "I'm having a hot flash now" or logging moods each evening). With or without active logging, the system collects continuous data and begins to apply algorithms to detect outliers or significant changes relative to moving averages. However, alerts may be suppressed or conservative during the calibration mode until enough data is gathered.

For each biometric signal, the system 300 computes baseline metrics. For example, it might calculate the user's average resting heart rate during sleep, average daytime heart rate, typical diurnal temperature variation (how much the user's skin temperature fluctuates normally over the course of 24 hours), and baseline HRV during deep sleep versus during stress. Baseline could be defined as a combination of central tendency (mean or median) and variability (standard deviation, etc.) for each metric in different contexts (rest vs activity, night vs day). The ambient environmental data is also factored in—for instance, the baseline skin temperature might be higher in a hot climate and that's normal for that user, so a "spike" must be judged relative to both the user's own range and possibly the ambient conditions.

During calibration, the system may also identify personal patterns. For example, perhaps the user's heart rate tends to jump when climbing stairs, or their wearable's temperature sensor reads a consistently higher absolute value than true core body temperature due to placement. The calibration algorithms can account for and filter out expected variations (like exercise or sensor noise), so they are not mistaken for symptom signatures. If the user is still menstruating irregularly (perimenopause), the calibration period also tracks cycle data to see if any physiological changes correlate with cycle phases.

At step 504 the system 300 configures the predictive model with the user's baseline circadian patterns and filters out routine activities to reduce false positive predictions. This personalized calibration data established in step 502, may then be used to set initial thresholds and model parameters. For instance, a generic model might consider a rise in skin temperature of 1° C. in 30 seconds to be significant for hot flash detection, but if a particular user's skin temp sometimes fluctuates that much normally (perhaps due to exercise or external heat exposure), the system will adjust to require a larger or differently patterned change for that user. The thresholds may be multivariate—e.g., requiring simultaneous changes in both HR and temp beyond certain degrees. These can also be dynamic thresholds that depend on context (like time of day or prior events).

Once the personalized biometric baseline is established, the system 300 may periodically update the personalized biometric baseline, based on more recently received biometric data, and contextual data.

At step 506 the system 300 obtains user feedback on the predicted menopause related symptom. In various embodiments, the system 300 obtains the user feedback after the system 300 detects the occurrence of the predicted menopause related symptom. In other embodiments, the system 300 obtains the user feedback after a preset time interval after the system 300 predicts the menopause related symptom. The interval may be personalized for the user, for example, based on the personalized biometric baseline.

The system 300 may prompt the user to provide a confirmation of occurrence or a severity rating of the predicted menopause related symptom. Next, the system 300 may receive the user feedback which includes the confirmation of occurrence and/or the severity rating of the predicted menopause related symptom. Next, the system 300 identifies the predicted menopause related symptom as a true positive or a false positive, or a false negative. Finally, the system 300 may update at least one of the personalized biometric baseline, and the predictive model, based on whether the symptom was identified as a true positive, a false positive, or a false negative.

For instance, after a predicted event, the app might display "We predicted you had a hot flash around 3:00 PM—did that feel accurate?" with options to confirm or dismiss. The user's response (and possibly the lack of a response) is fed back as a labeled outcome to continually refine the personal model. Over time, this supervised feedback loop can greatly increase personalized accuracy essentially performing ongoing calibration. If the user consistently reports false positives at certain times, the system readjusts to be less sensitive in those scenarios.

At step 508 the system 300 updates at least one of the personalized biometric baseline, and the predictive model, based on at least one of the plurality of biometric data streams, the detected pattern of physiological deviation, the predicted menopause related symptom, and the user feedback pertaining to the predicted menopause related symptom.

When implemented via computer-executable instructions, various elements of embodiments of the present disclosure are in essence the software code defining the operations of such various elements. The executable instructions or software code may be obtained from a tangible computer-readable medium (e.g., a hard drive media, optical media, EPROM, EEPROM, tape media, cartridge media, flash memory, ROM, memory stick, and/or the like). In fact, computer-readable media can include any medium that can store information.

FIG. 4 illustrates an example computer system 600 adapted according to one embodiment of the present disclosure. That is, computer system 600 comprises an example system on which embodiments of the present disclosure may be implemented (such as a handheld device, a desktop/laptop computer, or computer controlling a wall-sized screen). Central processing unit (CPU) 602 is coupled to a system bus. CPU 602 may be any general-purpose CPU. The present disclosure is not restricted by the architecture of CPU 602 as long as CPU 602 supports the inventive operations as described herein. CPU 602 may execute the various logical instructions according to embodiments of the present disclosure. For example, CPU 602 may execute machine-level instructions according to the exemplary operational flow described above in conjunction with FIGS. 3, 4 and 5.

Computer system 600 also preferably includes random access memory (RAM) 604, which may be SRAM, DRAM, SDRAM, or the like. Computer system 600 preferably includes read-only memory (ROM) 604, which may be PROM, EPROM, EEPROM, or the like. RAM 604 and ROM 606 hold user and system data and programs, as is well known in the art.

Computer system 600 also preferably includes input/output (I/O) adapter 608, network adaptor 610, user interface adapter 612, and display adapter 614. I/O adapter 608, user interface adapter 612, and/or network adaptor 610 may, in certain embodiments, enable a user to interact with computer system 600 in order to input information, such as receiving input from a touchscreen, keypad, mouse/touchpad/roller ball, displaying items on a screen, and the like.

I/O adapter 608 preferably connects to storage device(s), such as one or more of hard drive, solid state disk (SSD) drive, compact disc (CD) drive, floppy disk drive, tape drive, etc. to computer system 600. The storage devices may be utilized when RAM 604 is insufficient for the memory requirements associated with storing data. Network adaptor 610 is preferably adapted to couple computer system 600 to a network (e.g., a local area network, the Internet, a cellular phone network, and/or the like). User interface adapter 612 couples user input devices, such as a keyboard, a pointing device, and a microphone and/or output devices, such as speaker(s) to computer system 600. Display adapter 614 is driven by CPU 602 to control the display device 626 to, for example, display the user interface, which may include touchscreen capability.

It shall be appreciated that the present disclosure is not limited to the architecture of system 600. For example, any suitable processor-based device may be utilized, including without limitation, personal computers, laptop computers, handheld computing devices, computer workstations, and multi-processor servers. Moreover, embodiments of the present disclosure may be implemented on application specific integrated circuits (ASICs) or very large scale integrated (VLSI) circuits. In fact, persons of ordinary skill in the art may utilize any number of suitable structures capable of executing logical operations according to the embodiments of the present disclosure.

While the above descriptions focus primarily on predicting and managing vasomotor symptoms (hot flashes and night sweats), the invention can extend to other menopause-related conditions:

Mood and Cognitive Symptoms: Some embodiments may include tracking and predicting mood swings, anxiety, or cognitive fog which can accompany menopause. Wearable data such as sleep quality metrics and physiological stress indicators (e.g., HRV) combined with perhaps voice tone analysis or keystroke patterns on phone (if permitted) could help anticipate a mood drop or anxiety episode. Interventions might be a notification to practice a mindfulness exercise or alert a chosen friend/caregiver if severe.

Menstrual Irregularity and Cycle Transition: For women in early perimenopause, the system can monitor cycle length and ovulation patterns (using body temp and other fertility indicators from wearables) to predict when periods may become irregular or cease. An alert like "It has been 60 days since your last period; this could indicate the onset of menopause" could be given, prompting consultation with a doctor.

Bone Health and Metabolic Changes: Extended use of the system might integrate other health data (like activity levels contributing to bone density preservation, or weight/BMI changes) to give holistic guidance beyond immediate symptom relief.

Medication and Treatment Feedback: If a user starts a new menopause therapy (like Hormone Replacement Therapy, HRT), the system can help track its effectiveness by showing changes in the metrics (e.g., an improvement in sleep or reduction in hot flash frequency reflected in the data). This can be valuable information for the user and her healthcare provider, potentially shared in an aggregated report (with user permission).

The system architecture and methods described herein are applicable not only to menopause but to a broader class of hormone- or autonomic-related dysregulation conditions, including perimenopause, postpartum transition, and medication-induced vasomotor instability. Further, the system architecture and methods described herein may also be applicable to other endocrine, metabolic, or cognitive transitions characterized by cyclical hormonal or autonomic patterns, for example, sleep disruption, stress reactivity, or metabolic instability, using the same predictive logic and data-fusion approach.

The embodiments described herein are merely exemplary in nature. The features, elements or variations described herein may be used in any combination, to enable improved functionality over the products and solutions known in the art. The description of the embodiments presented herein shall not be considered limiting. Instead, the innovation is described in the appended claims, with implementation variations presented in the detailed description above.

The invention claimed is:

1. A method for predicting menopause-related symptoms using multi-modal data and providing interventions, the method comprising:

receiving a plurality of biometric data streams of a user, including physiological measurements including heart rate, heart rate variability, body temperature, and blood oxygen saturation;

receiving contextual data streams, including at least one of an ambient temperature, a time of day, a sleep stage information, and menstrual cycle information of the user;

receiving from the user, a journal input including textual information describing the user's feelings, and/or the user's environmental context information;

natural language processing the journal input, to identify natural language features including one or more of emotional tone, symptom-intensity descriptors, and temporal references; and accessing a personalized biometric baseline, wherein the personalized biometric baseline is previously established based on the plurality of biometric data streams;

monitoring the plurality of biometric data streams and contextual data streams for deviations from the personalized biometric baseline;

detecting, using a predictive model, a pattern of deviation from the personalized biometric baseline correlating with an impending menopause-related symptom;

predicting, based on detecting the pattern of deviation, and the natural language features identified from the journal input, an occurrence of the menopause-related symptom, a prediction horizon before the menopause-related symptom begins; and responsive to the predicting, initiating an intervention action, wherein the intervention action comprises at least one of: presenting to the user a notification of the predicted menopause-related symptom, transmitting a control signal to an external device to mitigate the menopause-related symptom, and presenting a recommendation to the user to perform a mitigating activity;

wherein the menopause-related symptom includes one of a hot flash, night sweat, insomnia or sleep disturbance, mood swing, anxiety episode, heart palpitations, and fatigue.

2. The method of claim 1, further comprising:

establishing the personalized biometric baseline in a calibration mode, wherein the calibration mode spans at least two days of data collection during which no menopause related symptoms are detected, and configuring the predictive model with the user's baseline circadian patterns and filtering out routine activities to reduce false positive predictions.

3. The method of claim 1, further comprising:

updating at least one of the personalized biometric baseline, and the predictive model, based on at least one of the plurality of biometric data streams, the contextual data streams, the detected pattern of physiological deviation, the predicted menopause related symptom, and a user feedback pertaining to the predicted menopause related symptom; and transmitting the update to the predictive model to a remote learning and management server.

4. The method of claim 1, further comprising:

retrieving the predictive model from a remote server;

determining updated model parameters of the predictive model, based on at least one of the plurality of biometric data streams, the detected pattern of physiological deviation, the predicted menopause related symptom, and a user feedback confirming or denying occurrence of the predicted menopause related symptom; and transmitting the updated model parameters to the remote server, wherein the predictive model is a machine learning model or an artificial intelligence model.

5. The method of claim 1, further comprising:

analyzing prior intervention actions associated with respective prior predictions of respective prior menopause related symptoms, and severity of the respective prior menopause related symptom;

based on the analyzing, identifying a recommended intervention action wherein the recommended intervention action is the prior intervention action with the least severity of the respective prior menopause related symptom; and updating the predictive model, based on the identifying.

6. The method of claim 1, further comprising:

prompting the user to provide a confirmation of occurrence or a severity rating of the predicted menopause related symptom;

receiving the user feedback comprising the confirmation of occurrence or the severity rating of the predicted menopause related symptom;

identifying the predicted menopause related symptom as a true positive or a false positive; and updating at least one of the personalized biometric baseline, and the predictive model, based on the identifying.

7. The method of claim 1 further comprising:

mapping the predicted symptom and the intervention action to corresponding ones of Current Procedural Terminology (CPT) codes;

generating documentation suitable for remote patient-monitoring reimbursement, wherein the documentation includes at least one of the biometric data streams, the contextual data streams, the menopause related symptom prediction, a user feedback on the menopause related symptom prediction, and a user compliance metric; and transmitting to a remote patient monitoring system, the generated documentation and the CPT codes.

8. The method of claim 1 further comprising:

selecting the intervention action from a plurality of prior intervention actions, wherein the selected intervention action is associated with the largest suppression of intensity of the menopause related symptom.

9. The method of claim 1, wherein:

the plurality of biometric data streams of a user further comprise biochemical measurements including hormone levels, including at least one of oestradiol, progesterone, luteinizing hormone, cortisol, or thyroid markers.

10. A system for predicting menopause-related symptoms using multi-modal data and providing interventions, the system comprising:

a biometric module configured to receive a plurality of biometric data streams of a user, including physiological measurements including heart rate, heart rate variability, body temperature, and blood oxygen saturation;

a context module configured to receive contextual data streams, including at least one of an ambient temperature, a time of day, a sleep stage information, and menstrual cycle information of the user;

a journal module configured to:

receive from the user, a journal input including textual information describing the user's feelings, and/or the user's environmental context information;

natural language process the journal input, to identify natural language features including one or more of emotional tone, symptom-intensity descriptors, and temporal references;

a prognostic module configured to:

access a personalized biometric baseline, wherein the personalized biometric baseline is previously established based on the plurality of biometric data streams;

monitor the plurality of biometric data streams and contextual data streams for deviations from the personalized biometric baseline;

detect, using a predictive model, a pattern of deviation from the personalized biometric baseline correlating with an impending menopause-related symptom;

predict, based on detecting the pattern of deviation, and the natural language features identified from the journal input, an occurrence of the menopause-related symptom a prediction horizon before the menopause-related symptom begins; and an intervention module configured to, responsive to the predicting, initiate an intervention action, wherein the intervention action comprises at least one of: presenting to the user a notification of the predicted menopause-related symptom, transmitting a control signal to an external device to mitigate the menopause-related symptom, and presenting a recommendation to the user to perform a mitigating activity;

wherein the menopause-related symptom includes one of a hot flash, night sweat, insomnia or sleep disturbance, mood swing, anxiety episode, heart palpitations, and fatigue.

11. The system of claim 10, further comprising a calibration module configured to:

establish the personalized biometric baseline in a calibration mode, wherein the calibration mode spans at least two days of data collection during which no menopause related symptoms are detected, and configure the predictive model with the user's baseline circadian patterns and filtering out routine activities to reduce false positive predictions.

12. The system of claim 10, further comprising an update module configured to:

update at least one of the personalized biometric baseline, and the predictive model, based on at least one of the plurality of biometric data streams, the detected pattern of physiological deviation, the predicted menopause related symptom, and a user feedback pertaining to the predicted menopause related symptom; and transmit the update to the predictive model to a remote learning and management server.

13. The system of claim 10, further comprising an update module configured to:

retrieve the predictive model from a remote server;

determine updated model parameters of the predictive model, based on at least one of the plurality of biometric data streams, the detected pattern of physiological deviation, the predicted menopause related symptom, and a user feedback confirming or denying occurrence of the predicted menopause related symptom; and transmit the updated model parameters to the remote server, wherein the predictive model is a machine learning model or an artificial intelligence model.

14. The system of claim 10, further comprising an update module configured to:

analyze prior intervention actions associated with respective prior predictions of respective prior menopause related symptoms, and severity of the respective prior menopause related symptom;

based on the analyzing, identify a recommended intervention action wherein the recommended intervention action is the prior intervention action with the least severity of the respective prior menopause related symptom; and update the predictive model, based on the identifying.

15. The system of claim 10, further comprising:

a user feedback module configured to:

prompt the user to provide a confirmation of occurrence or a severity rating of the predicted menopause related symptom;

receive the user feedback comprising the confirmation of occurrence or the severity rating of the predicted menopause related symptom;

identify the predicted menopause related symptom as a true positive or a false positive; and an update module configured to update at least one of the personalized biometric baseline, and the predictive model, based on the identifying.

16. The system of claim 10 further comprising a communication module configured to:

map the predicted symptom and the intervention action to corresponding ones of Current Procedural Terminology (CPT) codes;

generate documentation suitable for remote patient-monitoring reimbursement, wherein the documentation includes at least one of the biometric data streams, the contextual data streams, the menopause related symptom prediction, a user feedback on the menopause related symptom prediction, and a user compliance metric; and transmit to a remote patient monitoring system, the generated documentation and the CPT codes.

17. The system of claim 10, wherein the intervention module is further configured to:

select the intervention action from a plurality of prior intervention actions, wherein the selected intervention action is associated with the largest suppression of intensity of the menopause related symptom.

18. The system of claim 10, wherein:

the plurality of biometric data streams of a user further comprise biochemical measurements including hormone levels, including at least one of oestradiol, progesterone, luteinizing hormone, cortisol, or thyroid markers.

19. A computer program product comprising computer readable instructions stored on a non-transitory computer readable medium, the computer readable instructions when executed by a computer system comprising a processor, cause the processor to:

receive a plurality of biometric data streams of a user, including physiological measurements including heart rate, heart rate variability, body temperature, and blood oxygen saturation;

receive contextual data streams, including ambient temperature, and menstrual cycle information of the user;

receive from the user, a journal input including textual information describing the user's feelings, and/or the user's environmental context information;

natural language process the journal input, to identify natural language features including one or more of emotional tone, symptom-intensity descriptors, and temporal references;

access a personalized biometric baseline, wherein the personalized biometric baseline is previously established based on the plurality of biometric data streams;

monitor the plurality of biometric data streams and contextual data streams for deviations from the personalized biometric baseline;

detect, using a predictive model, a pattern of deviation from the personalized biometric baseline correlating with an impending menopause-related symptom;

predict, based on detecting the pattern of deviation, and the natural language features identified from the journal input, an occurrence of the menopause-related symptom a prediction horizon before the menopause related symptom begins; and responsive to the predicting, initiate an intervention action, wherein the intervention action comprises at least one of: presenting to the user a notification of the predicted menopause-related symptom, transmitting a control signal to an external device to mitigate the menopause-related symptom, and presenting a recommendation to the user to perform a mitigating activity;

wherein the menopause-related symptom includes one of a hot flash, night sweat, insomnia or sleep disturbance, mood swing, anxiety episode, heart palpitations, and fatigue.

20. The computer program product of claim 19, further comprising computer readable instructions that cause the processor to:

establish the personalized biometric baseline in a calibration mode, wherein the calibration mode spans at least two days of data collection during which no menopause related symptoms are detected, and configure the predictive model with the user's baseline circadian patterns and filtering out routine activities to reduce false positive predictions.

21. The computer program product of claim 19, further comprising computer readable instructions that cause the processor to:

update at least one of the personalized biometric baseline, and the predictive model, based on at least one of the plurality of biometric data streams, the detected pattern of physiological deviation, the predicted menopause related symptom, and a user feedback pertaining to the predicted menopause related symptom; and transmit the update to the predictive model to a remote learning and management server.

22. The computer program product of claim 21, further comprising computer readable instructions that cause the processor to:

select the intervention action from a plurality of prior intervention actions, wherein the selected intervention action is associated with the largest suppression of intensity of the menopause related symptom.

23. The computer program product of claim 19, further comprising computer readable instructions that cause the processor to:

retrieve the predictive model from a remote server;

determine updated model parameters of the predictive model, based on at least one of the plurality of biometric data streams, the detected pattern of physiological deviation, the predicted menopause related symptom, and a user feedback confirming or denying occurrence of the predicted menopause related symptom;

transmit the updated model parameters to the remote server, wherein the predictive model is a machine learning model or an artificial intelligence model.

24. The computer program product of claim 19, further comprising computer readable instructions that cause the processor to:

analyze prior intervention actions associated with respective prior predictions of respective prior menopause related symptoms, and severity of the respective prior menopause related symptom;

based on the analyzing, identify a recommended intervention action wherein the recommended intervention action is the prior intervention action with the least severity of the respective prior menopause related symptom; and update the predictive model, based on the identifying.

25. The computer program product of claim 19, further comprising computer readable instructions that cause the processor to:

prompt the user to provide a confirmation of occurrence or a severity rating of the predicted menopause related symptom;

receive the user feedback comprising the confirmation of occurrence or the severity rating of the predicted menopause related symptom;

identify the predicted menopause related symptom as a true positive or a false positive; and update at least one of the personalized biometric baseline, and the predictive model, based on the identifying.

26. The computer program product of claim 19, further comprising computer readable instructions that cause the processor to:

map the predicted symptom and the intervention action to corresponding ones of Current Procedural Terminology (CPT) codes;

generate documentation suitable for remote patient-monitoring reimbursement, wherein the documentation includes at least one of the biometric data streams, the contextual data streams, the menopause related symptom prediction, a user feedback on the menopause related symptom prediction, and a user compliance metric; and transmit to a remote patient monitoring system.

27. The computer program product of claim 19, wherein:

the plurality of biometric data streams of a user further comprise biochemical measurements including hormone levels, including at least one of oestradiol, progesterone, luteinizing hormone, cortisol, or thyroid markers.

* * * * *